United States Patent
Reitblat et al.

(10) Patent No.: US 10,912,590 B2
(45) Date of Patent: *Feb. 9, 2021

(54) PERCUTANEOUS SPINAL CROSS LINK SYSTEM AND METHOD

(71) Applicant: Stryker European Operations Holdings LLC, Kalamazoo, MI (US)

(72) Inventors: Abram Reitblat, Monroe, NY (US); Lori Dombrowski, Elmwood Park, NJ (US); Charles L. Bush, Jr., Wayne, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 96 days.

This patent is subject to a terminal disclaimer.

(21) Appl. No.: 15/797,592

(22) Filed: Oct. 30, 2017

(65) Prior Publication Data

US 2018/0064470 A1    Mar. 8, 2018

Related U.S. Application Data

(63) Continuation of application No. 14/201,213, filed on Mar. 7, 2014, now Pat. No. 9,827,020.
(Continued)

(51) Int. Cl.
*A61B 17/00* (2006.01)
*A61B 17/02* (2006.01)
(Continued)

(52) U.S. Cl.
CPC ........ *A61B 17/7049* (2013.01); *A61B 17/162* (2013.01); *A61B 17/1671* (2013.01);
(Continued)

(58) Field of Classification Search
CPC .............. A61B 17/7049; A61B 17/162; A61B 17/1671; A61B 17/7076; A61B 17/7085;
(Continued)

(56) References Cited

U.S. PATENT DOCUMENTS

| 3,788,318 A | 1/1974 | Kim et al. |
| 3,789,852 A | 2/1974 | Kim et al. |

(Continued)

FOREIGN PATENT DOCUMENTS

| DE | 3711091 | 10/1988 |
| DE | 4238339 A1 | 5/1994 |

(Continued)

OTHER PUBLICATIONS

Bare Bones; Monthly Executive Summary, vol. 12, No. 1, p. 1-4, Jan. 2003.

(Continued)

*Primary Examiner* — Pedro Philogene
(74) *Attorney, Agent, or Firm* — Lerner, David, Littenberg, Krumholz & Mentlik, LLP

(57) ABSTRACT

A percutaneous spinal cross link system for interconnecting a spinal fusion construct on one side of the longitudinal axis of the spine with a spinal fusion construct on the other side of the longitudinal axis may include a cross bar connected at each end by a respective connector to a respective spinal fusion rod of each of the spinal fusion constructs. The connector may include a rod receiving portion adapted to receive one of the spinal fusion rods and a cross bar receiving portion adapted to receive the cross bar in an orientation generally perpendicular to the spinal fusion rod. A cannula defined by two spaced apart blades may be connected to the connector for defining a minimally invasive pathway through body tissue for introduction of the cross bar to the connector. Other tools for use with the system are also disclosed.

11 Claims, 13 Drawing Sheets

Related U.S. Application Data

(60) Provisional application No. 61/782,278, filed on Mar. 14, 2013.

(51) Int. Cl.
    *A61B 17/16*     (2006.01)
    *A61B 17/70*     (2006.01)
    *A61B 17/88*     (2006.01)
    *A61B 90/00*     (2016.01)

(52) U.S. Cl.
    CPC ...... *A61B 17/7076* (2013.01); *A61B 17/7085* (2013.01); *A61B 17/7086* (2013.01); *A61B 17/7091* (2013.01); *A61B 17/8863* (2013.01); *A61B 17/0218* (2013.01); *A61B 2017/0046* (2013.01); *A61B 2090/037* (2016.02)

(58) Field of Classification Search
    CPC ............ A61B 17/7086; A61B 17/7091; A61B 17/8863; A61B 17/0218; A61B 2090/037; A61B 2017/0046
    USPC ........... 606/246–289, 86 A, 90, 99, 907–914
    See application file for complete search history.

(56) References Cited

U.S. PATENT DOCUMENTS

| | | |
|---|---|---|
| 3,892,232 A | 7/1975 | Neufeld |
| 4,083,370 A | 4/1978 | Taylor |
| 4,269,184 A | 5/1981 | Montgomery |
| 4,350,151 A | 9/1982 | Scott |
| 4,409,968 A | 10/1983 | Drummond |
| 4,411,259 A | 10/1983 | Drummond |
| 4,448,191 A | 5/1984 | Rodnyansky et al. |
| 4,449,532 A | 5/1984 | Storz |
| 4,474,046 A | 10/1984 | Cook |
| 4,545,374 A | 10/1985 | Jacobson |
| 4,562,832 A | 1/1986 | Wilder et al. |
| 4,611,581 A | 9/1986 | Steffee |
| 4,653,481 A | 3/1987 | Howland et al. |
| 4,790,297 A | 12/1988 | Luque |
| 4,817,587 A | 4/1989 | Janese |
| 4,862,891 A | 9/1989 | Smith |
| 4,887,595 A | 12/1989 | Heinig et al. |
| 4,899,729 A | 2/1990 | Gill et al. |
| 4,913,134 A | 4/1990 | Luque |
| 4,957,495 A | 9/1990 | Kluger |
| 4,984,564 A | 1/1991 | Yuen |
| 5,010,879 A | 4/1991 | Moriya et al. |
| 5,027,793 A | 7/1991 | Engelhardt et al. |
| 5,035,232 A | 7/1991 | Lutze et al. |
| 5,125,396 A | 6/1992 | Ray |
| 5,139,487 A | 8/1992 | Baber |
| 5,171,279 A | 12/1992 | Mathews |
| 5,183,464 A | 2/1993 | Dubrul et al. |
| 5,195,541 A | 3/1993 | Obenchain |
| 5,197,971 A | 3/1993 | Bonutti |
| 5,242,443 A | 9/1993 | Kambin |
| 5,293,863 A | 3/1994 | Zhu et al. |
| 5,295,994 A | 3/1994 | Bonutti |
| D346,217 S | 4/1994 | Sparker et al. |
| 5,312,417 A | 5/1994 | Wilk |
| 5,357,983 A | 10/1994 | Mathews |
| 5,360,431 A | 11/1994 | Puno et al. |
| 5,373,860 A | 12/1994 | Catone |
| 5,377,667 A | 1/1995 | Patton et al. |
| 5,381,788 A | 1/1995 | Matula et al. |
| 5,395,317 A | 3/1995 | Kambin |
| 5,409,488 A | 4/1995 | Ulrich |
| 5,425,732 A | 6/1995 | Ulrich |
| 5,439,464 A | 8/1995 | Shapiro |
| 5,454,365 A | 10/1995 | Bonutti |
| 5,464,011 A | 11/1995 | Bridge |
| 5,480,440 A | 1/1996 | Kambin |
| 5,490,409 A | 2/1996 | Weber |
| 5,496,322 A | 3/1996 | Mathews |
| 5,545,228 A | 8/1996 | Kambin |
| 5,569,248 A | 10/1996 | Mathews |
| 5,569,290 A | 10/1996 | McAfee |
| 5,584,887 A | 12/1996 | Kambin |
| 5,591,165 A | 1/1997 | Jackson |
| 5,601,562 A | 2/1997 | Wolf et al. |
| 5,601,590 A | 2/1997 | Bonutti et al. |
| 5,624,442 A | 4/1997 | Mellinger et al. |
| 5,658,286 A | 8/1997 | Sava |
| 5,707,359 A | 1/1998 | Bufalini |
| 5,720,751 A | 2/1998 | Jackson |
| 5,728,097 A | 3/1998 | Mathews |
| 5,741,261 A | 4/1998 | Moskovitz et al. |
| 5,743,907 A | 4/1998 | Asher et al. |
| 5,746,720 A | 5/1998 | Stouder, Jr. |
| 5,762,629 A | 6/1998 | Kambin |
| 5,772,594 A | 6/1998 | Barrick |
| 5,792,044 A | 8/1998 | Foley et al. |
| 5,795,289 A | 8/1998 | Wyttenbach |
| 5,814,046 A | 9/1998 | Hopf et al. |
| 5,882,344 A | 3/1999 | Stouder, Jr. |
| 5,885,291 A | 3/1999 | Moskovitz et al. |
| 5,885,292 A | 3/1999 | Moskovitz et al. |
| 5,891,147 A | 4/1999 | Moskovitz et al. |
| 5,902,231 A | 5/1999 | Foley et al. |
| RE36,221 E | 6/1999 | Breard et al. |
| 5,928,139 A | 7/1999 | Koros et al. |
| 5,938,662 A | 8/1999 | Rinner |
| 5,944,658 A | 8/1999 | Koros et al. |
| 5,954,635 A | 9/1999 | Foley et al. |
| 5,957,888 A | 9/1999 | Hinchliffe |
| 5,961,499 A | 10/1999 | Bonutti et al. |
| 5,964,761 A | 10/1999 | Kambin |
| 5,976,146 A | 11/1999 | Ogawa et al. |
| 6,007,487 A | 12/1999 | Foley et al. |
| 6,015,409 A | 1/2000 | Jackson |
| 6,033,406 A | 3/2000 | Mathews |
| 6,035,691 A | 3/2000 | Lin et al. |
| 6,036,692 A | 3/2000 | Burel et al. |
| 6,080,156 A | 6/2000 | Asher et al. |
| 6,090,113 A | 7/2000 | Le Couedic et al. |
| 6,096,042 A | 8/2000 | Herbert |
| 6,123,707 A | 9/2000 | Wagner |
| 6,127,597 A | 10/2000 | Beyar et al. |
| 6,152,871 A | 11/2000 | Foley et al. |
| 6,159,179 A | 12/2000 | Simonson |
| 6,162,170 A | 12/2000 | Foley et al. |
| 6,175,758 B1 | 1/2001 | Kambin |
| 6,176,823 B1 | 1/2001 | Foley et al. |
| 6,183,472 B1 | 2/2001 | Lutz |
| 6,187,000 B1 | 2/2001 | Davison et al. |
| 6,197,002 B1 | 3/2001 | Peterson |
| 6,200,322 B1 | 3/2001 | Branch et al. |
| 6,206,822 B1 | 3/2001 | Foley et al. |
| 6,206,826 B1 | 3/2001 | Mathews et al. |
| 6,217,509 B1 | 4/2001 | Foley et al. |
| 6,226,548 B1 | 5/2001 | Foley et al. |
| 6,235,028 B1 | 5/2001 | Brumfield et al. |
| 6,287,313 B1 | 9/2001 | Sasso |
| 6,332,780 B1 | 12/2001 | Traxel et al. |
| 6,338,730 B1 | 1/2002 | Bonutti et al. |
| 6,358,266 B1 | 3/2002 | Bonutti |
| 6,368,320 B1 | 4/2002 | Le Couedic et al. |
| 6,371,968 B1 | 4/2002 | Kogasaka et al. |
| 6,425,859 B1 | 7/2002 | Foley et al. |
| 6,475,218 B2 | 11/2002 | Gournay et al. |
| 6,485,518 B1 | 11/2002 | Cornwall et al. |
| 6,506,151 B2 | 1/2003 | Estes et al. |
| 6,520,907 B1 | 2/2003 | Foley et al. |
| 6,524,320 B2 | 2/2003 | DiPoto |
| 6,530,926 B1 | 3/2003 | Davison |
| 6,530,929 B1 | 3/2003 | Justis et al. |
| 6,558,386 B1 | 5/2003 | Cragg |
| 6,558,390 B2 | 5/2003 | Cragg |
| 6,562,046 B2 | 5/2003 | Sasso |
| 6,575,979 B1 | 6/2003 | Cragg |
| 6,596,008 B1 | 7/2003 | Kambin |
| 6,605,095 B2 | 8/2003 | Grossman |

(56) References Cited

U.S. PATENT DOCUMENTS

| | | | |
|---|---|---|---|
| 6,607,530 B1 | 8/2003 | Carl et al. | |
| 6,613,050 B1 | 9/2003 | Wagner et al. | |
| 6,648,888 B1 | 11/2003 | Shluzas | |
| 6,652,553 B2 | 11/2003 | Davison et al. | |
| 6,660,006 B2 | 12/2003 | Markworth et al. | |
| 6,692,434 B2 | 2/2004 | Ritland | |
| 6,692,473 B2 | 2/2004 | St. Cyr et al. | |
| 6,723,095 B2 | 4/2004 | Hammerslag | |
| 6,740,089 B2 | 5/2004 | Haider | |
| 6,740,090 B1 | 5/2004 | Cragg et al. | |
| 6,746,449 B2 | 6/2004 | Jones et al. | |
| 6,749,614 B2 | 6/2004 | Teitelbaum et al. | |
| 6,770,074 B2 | 8/2004 | Michelson | |
| 6,790,210 B1 | 9/2004 | Cragg et al. | |
| 6,793,656 B1 | 9/2004 | Mathews | |
| 6,800,084 B2 | 10/2004 | Davison et al. | |
| 6,811,558 B2 | 11/2004 | Davison et al. | |
| 6,821,277 B2 | 11/2004 | Teitelbaum | |
| 6,837,891 B2 | 1/2005 | Davison et al. | |
| 6,849,064 B2 | 2/2005 | Hamada | |
| 6,875,212 B2 | 4/2005 | Shaolian et al. | |
| 6,899,713 B2 | 5/2005 | Shaolian et al. | |
| 6,923,811 B1 | 8/2005 | Carl et al. | |
| 6,929,647 B2 | 8/2005 | Cohen | |
| 6,964,667 B2 | 11/2005 | Shaolian et al. | |
| 7,008,422 B2 | 3/2006 | Foley et al. | |
| 7,008,424 B2 | 3/2006 | Teitelbaum | |
| 7,011,660 B2 | 3/2006 | Sherman et al. | |
| 7,083,621 B2 | 8/2006 | Shaolian et al. | |
| 7,160,300 B2 | 1/2007 | Jackson | |
| 7,188,626 B2 | 3/2007 | Foley et al. | |
| 7,250,052 B2 | 7/2007 | Landry et al. | |
| 7,261,714 B2 | 8/2007 | Richelsoph | |
| 7,306,603 B2 | 12/2007 | Boehm, Jr. et al. | |
| 7,491,218 B2 | 2/2009 | Landry et al. | |
| 7,699,873 B2 | 4/2010 | Stevenson et al. | |
| 7,758,617 B2 | 7/2010 | Iott et al. | |
| 7,811,288 B2 | 10/2010 | Jones et al. | |
| 7,842,073 B2 | 11/2010 | Richelsoph et al. | |
| 7,909,830 B2 * | 3/2011 | Frigg | A61B 17/7002 606/104 |
| 7,914,558 B2 * | 3/2011 | Landry | A61B 17/1604 606/246 |
| 7,927,360 B2 | 4/2011 | Pond, Jr. et al. | |
| 7,955,355 B2 | 6/2011 | Chin | |
| 8,002,798 B2 | 8/2011 | Chin et al. | |
| 8,105,361 B2 | 1/2012 | Anderson et al. | |
| 8,157,809 B2 | 4/2012 | Butters et al. | |
| 8,177,817 B2 | 5/2012 | Fallin | |
| 8,192,440 B2 | 6/2012 | Jones et al. | |
| 8,394,109 B2 | 3/2013 | Hutton et al. | |
| 8,894,655 B2 | 11/2014 | Fallin et al. | |
| 9,198,698 B1 * | 12/2015 | Doose | A61B 17/7082 |
| 10,206,723 B2 * | 2/2019 | Stein | A61B 17/7083 |
| 2001/0011170 A1 | 8/2001 | Davison et al. | |
| 2001/0027320 A1 | 10/2001 | Sasso | |
| 2001/0029353 A1 | 10/2001 | Peterson | |
| 2001/0049498 A1 | 12/2001 | Davison et al. | |
| 2001/0049527 A1 | 12/2001 | Cragg | |
| 2001/0053915 A1 | 12/2001 | Grossman | |
| 2002/0016583 A1 | 2/2002 | Cragg | |
| 2002/0045904 A1 | 4/2002 | Fuss et al. | |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0107519 A1 | 8/2002 | Dixon et al. | |
| 2002/0116006 A1 | 8/2002 | Cohen | |
| 2002/0161367 A1 | 10/2002 | Ferree | |
| 2002/0161368 A1 | 10/2002 | Foley et al. | |
| 2002/0173796 A1 | 11/2002 | Cragg | |
| 2002/0183758 A1 | 12/2002 | Middleton et al. | |
| 2002/0198526 A1 | 12/2002 | Shaolian et al. | |
| 2003/0004517 A1 | 1/2003 | Anderson | |
| 2003/0009172 A1 | 1/2003 | Bonutti | |
| 2003/0060824 A1 | 3/2003 | Viart et al. | |
| 2003/0060826 A1 | 3/2003 | Foley et al. | |
| 2003/0073998 A1 | 4/2003 | Pagliuca et al. | |
| 2003/0083688 A1 * | 5/2003 | Simonson | A61B 17/0218 606/191 |
| 2003/0139648 A1 | 7/2003 | Foley et al. | |
| 2003/0191474 A1 | 10/2003 | Cragg et al. | |
| 2003/0195518 A1 | 10/2003 | Cragg | |
| 2003/0199871 A1 | 10/2003 | Foley et al. | |
| 2003/0199872 A1 | 10/2003 | Markworth et al. | |
| 2003/0199884 A1 | 10/2003 | Davison et al. | |
| 2003/0204189 A1 | 10/2003 | Cragg | |
| 2003/0208202 A1 | 11/2003 | Falahee | |
| 2003/0225408 A1 | 12/2003 | Nichols et al. | |
| 2003/0229353 A1 | 12/2003 | Cragg | |
| 2004/0006341 A1 | 1/2004 | Shaolian et al. | |
| 2004/0006344 A1 | 1/2004 | Nguyen et al. | |
| 2004/0034351 A1 | 2/2004 | Sherman et al. | |
| 2004/0039384 A1 | 2/2004 | Boehm et al. | |
| 2004/0059333 A1 | 3/2004 | Carl et al. | |
| 2004/0082954 A1 | 4/2004 | Teitelbaum et al. | |
| 2004/0082960 A1 | 4/2004 | Davison | |
| 2004/0082961 A1 | 4/2004 | Teitelbaum | |
| 2004/0087950 A1 | 5/2004 | Teitelbaum | |
| 2004/0092934 A1 | 5/2004 | Howland | |
| 2004/0093001 A1 | 5/2004 | Hamada | |
| 2004/0106934 A1 | 6/2004 | Grossman | |
| 2004/0133201 A1 | 7/2004 | Shluzas et al. | |
| 2004/0138662 A1 | 7/2004 | Landry et al. | |
| 2004/0143265 A1 | 7/2004 | Landry et al. | |
| 2004/0143268 A1 | 7/2004 | Falahee | |
| 2004/0147928 A1 | 7/2004 | Landry et al. | |
| 2004/0147936 A1 | 7/2004 | Rosenberg et al. | |
| 2004/0162560 A1 | 8/2004 | Raynor et al. | |
| 2004/0172022 A1 | 9/2004 | Landry et al. | |
| 2004/0176763 A1 | 9/2004 | Foley et al. | |
| 2004/0194791 A1 | 10/2004 | Sterman et al. | |
| 2004/0215190 A1 | 10/2004 | Nguyen et al. | |
| 2004/0215193 A1 | 10/2004 | Shaolian et al. | |
| 2004/0236317 A1 | 11/2004 | Davison | |
| 2004/0254576 A1 | 12/2004 | Dunbar et al. | |
| 2004/0260287 A1 | 12/2004 | Ferree | |
| 2004/0267279 A1 | 12/2004 | Casutt et al. | |
| 2005/0010220 A1 | 1/2005 | Casutt et al. | |
| 2005/0010221 A1 | 1/2005 | Dalton | |
| 2005/0021030 A1 | 1/2005 | Pagliuca et al. | |
| 2005/0021031 A1 | 1/2005 | Foley et al. | |
| 2005/0025771 A1 | 2/2005 | Wagner | |
| 2005/0033297 A1 | 2/2005 | Davison | |
| 2005/0038432 A1 | 2/2005 | Shaolian et al. | |
| 2005/0038434 A1 | 2/2005 | Mathews | |
| 2005/0043741 A1 | 2/2005 | Michelson | |
| 2005/0043742 A1 | 2/2005 | Bruneau et al. | |
| 2005/0059969 A1 | 3/2005 | McKinley | |
| 2005/0065515 A1 | 3/2005 | Jahng | |
| 2005/0065517 A1 | 3/2005 | Chin | |
| 2005/0070917 A1 | 3/2005 | Justis | |
| 2005/0080418 A1 | 4/2005 | Simonson et al. | |
| 2005/0085813 A1 | 4/2005 | Spitler et al. | |
| 2005/0090822 A1 | 4/2005 | DiPoto | |
| 2005/0090833 A1 | 4/2005 | DiPoto | |
| 2005/0113833 A1 | 5/2005 | Davison | |
| 2005/0124991 A1 | 6/2005 | Jahng | |
| 2005/0131407 A1 | 6/2005 | Sicvol et al. | |
| 2005/0131408 A1 | 6/2005 | Sicvol et al. | |
| 2005/0131421 A1 | 6/2005 | Anderson et al. | |
| 2005/0131422 A1 | 6/2005 | Anderson et al. | |
| 2005/0137461 A1 | 6/2005 | Marchek et al. | |
| 2005/0137593 A1 | 6/2005 | Gray et al. | |
| 2005/0149022 A1 | 7/2005 | Shaolian et al. | |
| 2005/0149035 A1 | 7/2005 | Pimenta et al. | |
| 2005/0154389 A1 | 7/2005 | Selover et al. | |
| 2005/0165396 A1 | 7/2005 | Fortin et al. | |
| 2005/0171540 A1 | 8/2005 | Lim et al. | |
| 2005/0182410 A1 | 8/2005 | Jackson | |
| 2005/0192570 A1 | 9/2005 | Jackson | |
| 2005/0245928 A1 | 11/2005 | Colleran et al. | |
| 2005/0251139 A1 | 11/2005 | Roh | |
| 2005/0277928 A1 | 12/2005 | Boschert | |
| 2005/0277934 A1 | 12/2005 | Vardiman | |

(56) References Cited

U.S. PATENT DOCUMENTS

| | | |
|---|---|---|
| 2005/0277942 A1 | 12/2005 | Kullas et al. |
| 2006/0030839 A1* | 2/2006 | Park .................. A61B 17/7032 606/1 |
| 2006/0030858 A1 | 2/2006 | Simonson et al. |
| 2006/0030861 A1 | 2/2006 | Simonson et al. |
| 2006/0036252 A1 | 2/2006 | Baynham et al. |
| 2006/0084980 A1 | 4/2006 | Melkent et al. |
| 2006/0111713 A1 | 5/2006 | Jackson |
| 2006/0111714 A1 | 5/2006 | Foley |
| 2006/0111715 A1 | 5/2006 | Jackson |
| 2006/0161157 A1 | 7/2006 | Mosca et al. |
| 2006/0200135 A1 | 9/2006 | Sherman et al. |
| 2006/0217735 A1 | 9/2006 | MacDonald et al. |
| 2006/0247658 A1 | 11/2006 | Pond et al. |
| 2006/0264934 A1 | 11/2006 | Fallin |
| 2006/0264962 A1* | 11/2006 | Chin .................. A61B 17/7037 606/90 |
| 2006/0293680 A1 | 12/2006 | Jackson |
| 2007/0043359 A1 | 2/2007 | Altarac et al. |
| 2007/0078460 A1 | 4/2007 | Frigg et al. |
| 2007/0083210 A1 | 4/2007 | Hestad et al. |
| 2007/0093824 A1 | 4/2007 | Hestad et al. |
| 2007/0118120 A1 | 5/2007 | Stevenson et al. |
| 2007/0270817 A1 | 11/2007 | Rezach |
| 2008/0009864 A1 | 1/2008 | Forton et al. |
| 2008/0125789 A1 | 5/2008 | Butters et al. |
| 2008/0125817 A1 | 5/2008 | Arnett et al. |
| 2008/0154280 A1 | 6/2008 | Schumacher et al. |
| 2008/0300638 A1 | 12/2008 | Beardsley et al. |
| 2008/0312655 A1 | 12/2008 | Kirschman et al. |
| 2009/0099605 A1* | 4/2009 | Fallin .................. A61B 17/7085 606/252 |
| 2009/0156902 A1 | 6/2009 | Dewey et al. |
| 2009/0171391 A1* | 7/2009 | Hutton .............. A61B 17/7032 606/246 |
| 2009/0177202 A1 | 7/2009 | May et al. |
| 2009/0210007 A1 | 8/2009 | Levy et al. |
| 2009/0216328 A1 | 8/2009 | Birkmeyer et al. |
| 2009/0228056 A1 | 9/2009 | Jackson |
| 2010/0049252 A1 | 2/2010 | Smisson, III et al. |
| 2010/0137915 A1 | 6/2010 | Anderson et al. |
| 2010/0160981 A1 | 6/2010 | Butler et al. |
| 2010/0331901 A1 | 12/2010 | Iott et al. |
| 2011/0015678 A1 | 1/2011 | Jackson |
| 2011/0077692 A1 | 3/2011 | Jackson |
| 2011/0152940 A1 | 6/2011 | Frigg et al. |
| 2011/0202095 A1 | 8/2011 | Semler et al. |
| 2011/0238120 A1 | 9/2011 | Chin |
| 2011/0245884 A9 | 10/2011 | Brumfield et al. |
| 2012/0089191 A1 | 4/2012 | Altarac et al. |
| 2012/0109202 A1 | 5/2012 | Kretzer et al. |
| 2012/0123477 A1 | 5/2012 | Landry et al. |
| 2012/0158070 A1 | 6/2012 | Jackson |
| 2012/0197302 A1 | 8/2012 | Fallin |
| 2012/0232593 A1 | 9/2012 | Predick |
| 2013/0030470 A1 | 1/2013 | Karas et al. |
| 2013/0096635 A1 | 4/2013 | Wall et al. |
| 2016/0175014 A1 | 6/2016 | Albert et al. |

FOREIGN PATENT DOCUMENTS

| | | |
|---|---|---|
| DE | 29710979 U1 | 8/1997 |
| DE | 19726754 A1 | 2/1999 |
| DE | 10027988 | 1/2002 |
| EP | 0528177 | 2/1993 |
| EP | 0528562 | 2/1993 |
| EP | 0611116 | 8/1994 |
| EP | 0665731 | 8/1995 |
| EP | 1006888 | 6/2000 |
| EP | 1027988 | 8/2000 |
| EP | 1248568 | 10/2002 |
| EP | 1374786 | 1/2004 |
| EP | 1468652 | 10/2004 |
| EP | 1545355 | 6/2005 |
| EP | 2356944 Z1 | 8/2011 |
| JP | 2003-511190 A | 3/2003 |
| JP | 2006-504505 A | 2/2006 |
| JP | 2011500267 A | 1/2011 |
| SU | 839513 | 6/1981 |
| WO | 93/18722 | 9/1993 |
| WO | 9409726 | 5/1994 |
| WO | 9514437 | 6/1995 |
| WO | 97/14457 | 4/1997 |
| WO | 9822030 A1 | 5/1998 |
| WO | 98/36785 | 8/1998 |
| WO | 98/38918 | 9/1998 |
| WO | 99/29242 | 6/1999 |
| WO | 99/511391 | 10/1999 |
| WO | 00/45720 | 8/2000 |
| WO | 01/012060 | 2/2001 |
| WO | 01/037744 | 5/2001 |
| WO | 0141681 A1 | 6/2001 |
| WO | 01/056479 | 8/2001 |
| WO | 01/060232 | 8/2001 |
| WO | 01/060234 | 8/2001 |
| WO | 01/060262 | 8/2001 |
| WO | 01/060263 | 8/2001 |
| WO | 01/060270 | 8/2001 |
| WO | 01/095823 | 12/2001 |
| WO | 02/085217 | 10/2002 |
| WO | 03020110 | 3/2003 |
| WO | 03028566 | 4/2003 |
| WO | 03/037170 | 5/2003 |
| WO | 03/057055 | 7/2003 |
| WO | 03/079914 | 10/2003 |
| WO | 03/088810 | 10/2003 |
| WO | 03/088878 | 10/2003 |
| WO | 04004584 | 1/2004 |
| WO | 04017847 | 3/2004 |
| WO | 04021899 | 3/2004 |
| WO | 04/028382 | 4/2004 |
| WO | 04/037070 | 5/2004 |
| WO | 04037074 | 5/2004 |
| WO | 04041100 | 5/2004 |
| WO | 2004058045 | 7/2004 |
| WO | 04080318 A1 | 9/2004 |
| WO | 05018466 | 3/2005 |
| WO | 05023123 | 3/2005 |
| WO | 2005020832 A1 | 3/2005 |
| WO | 05032358 | 4/2005 |
| WO | 05060534 A | 7/2005 |
| WO | 05072081 | 8/2005 |
| WO | 06/125029 | 11/2006 |
| WO | 06116662 | 11/2006 |

OTHER PUBLICATIONS

Diapason, Surgical Texchnique Catalog, Diapasan Spinal System, Jan. 2002.

Encore Spine; Degenerative System, Encore Surgical Product Brochure, p. 1-6, Oct. 2002.

Kambin et al, "Percutaneous Posterolateral Lumbar Discectomy and Decompression with a 6.9-millimeter cannula", the Journal of Bone and Joint Surgery, pp. 822-831, Jul. 1991.

Kambin et al., Anterior Column Support for Failed Fusion, Revision Spine Surgery, pp. 589-600, published Jan. 1999.

Kambin, "Arthroscopic Microdiscectomy", the Journal of Arthroscopy, vol. 8, No. 3, pp. 287-295, Sep. 1992.

Kambin, "Arthroscopic Microdiskectomy", the Mount Sinai Journal of Medicine, vol. 58, No. 2, Mar. 1991, pp. 159-164.

Kambin, "Posterolateral Percutaneous suction-excision of herniated lumbar intervertebral discs", Clinical Orthopaedics and Related Research. No. 207, pp. 37-42, Jun. 1988.

Kambin, Arthroscopic Lumbar Intervertebral Fusion, Chapter 95, the Adult Spine, vol. 2, pp. 2037-2046, Jan. 1997.

Kambin, Minimally Invasive Techniques in Spinal Surgery Current Practice, Neurosurgical Focus, wwwspineuniversecom, 16 pages, printed Aug. 24, 2005.

Kambin, Posterolateral Percutaneous Lumbar Discectomy and Decompression Arthroscopic Microdiscectomy, Section IV. pp. 67-100, Jan. 1991.

(56) References Cited

OTHER PUBLICATIONS

Kambin, Posterolateral Percutaneous Lumbar Interbody Fusion, Arthroscopic Microdiscectomy, pp. 117-121, Jan. 1991.
Kambin, The Role of Minimally Invasive Surgery in Spinal Disorders, Advance Operative Orthopedics, vol. 3, pp. 147-171, Dec. 1994.
Leu et al., Percutaneous Fusion of the Lumbar Spine, State of the Art Reviews, vol. 6, No. 3, pp. 593-604, Sep. 1992.
Maxcess; XLIF 90° Surgical Technique. Nuvasive Creative Spine Technology Product Brochure, p. 1-26, 2005.
Moss Miami Surgical Texhnique, DePuy, 14 pages, 1998.
Nex-Link; Spinal Fixation System, Spinal Concepts Web Page information, 1 page, "(retrieved Mar. 25, 2005)".
Partial European Search Report for Application No. EP14159769 dated Jun. 27, 2014.
Pathfinder; Minimally Invasive Pedicie Fixation System. Spinal Concepts Product Brochure p. 1-4, May 2003.
Smith and Nephew; 6.5mm and 4.0mm Cannulated Screws, Surgical Technique, p. 1-24, 1998.
Sofamor Danek; Eclipse CD Horizon Eclipse Implants and Instruments, Information from the Sofamor Danek Web page, p. 1-3, printed Mar. 29, 2005.
Sofamor Danek; Metrx, X-Tube, Refraction System; Sofamor Danek Web page information p. 1-2, printed Mar. 29, 2005.
Sofamor Danek; Sextant CD Horizon Sextant Rod Insertion System, Surgical Technique, Techniques, p. 1-29, 2003.
Spinal Concepts; Access Dilation Port, Spinal Concepts Web Page information 2 pages, 2004.
Canadian Examination Report for Application No. 2980049 dated Sep. 5, 2019, 3 pages.

\* cited by examiner

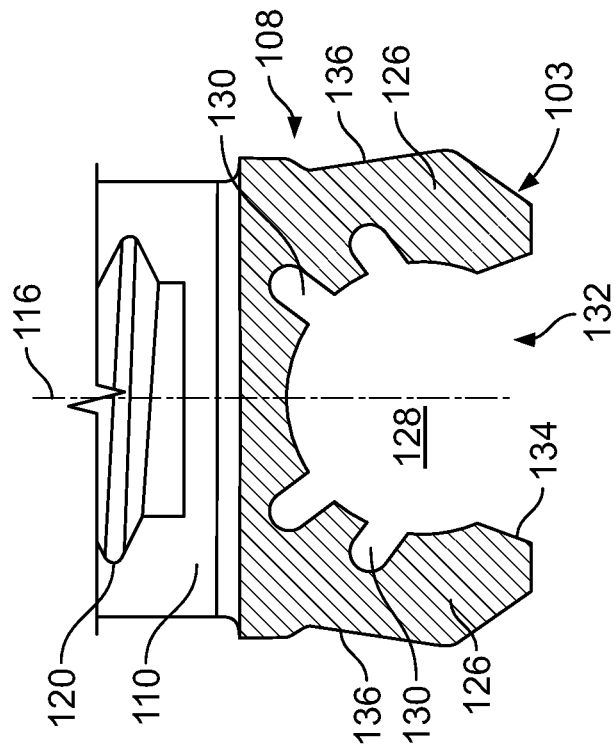
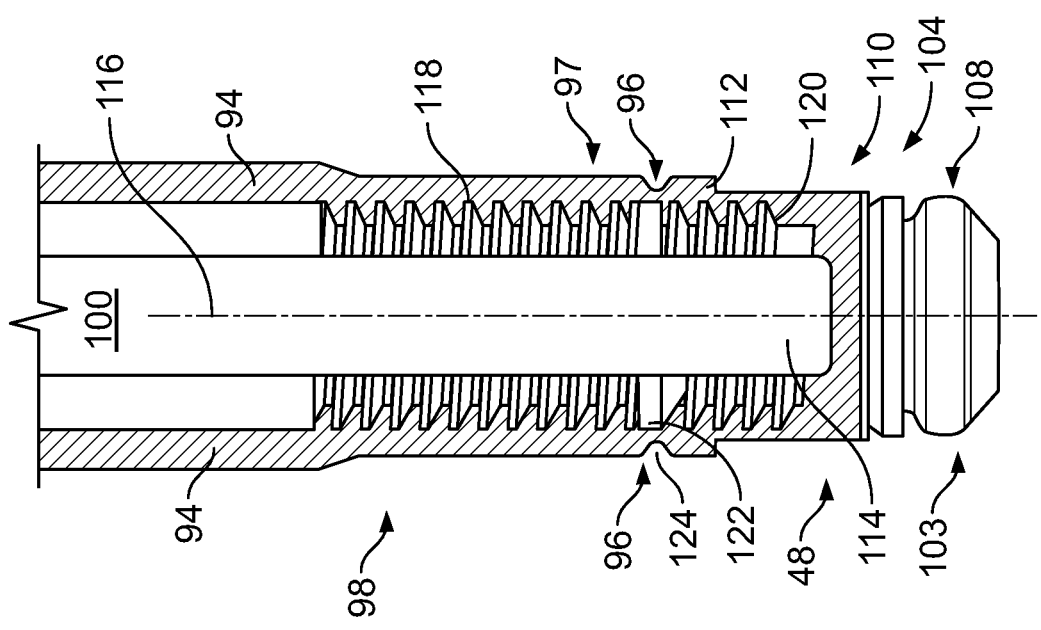
FIG. 6B
FIG. 6A

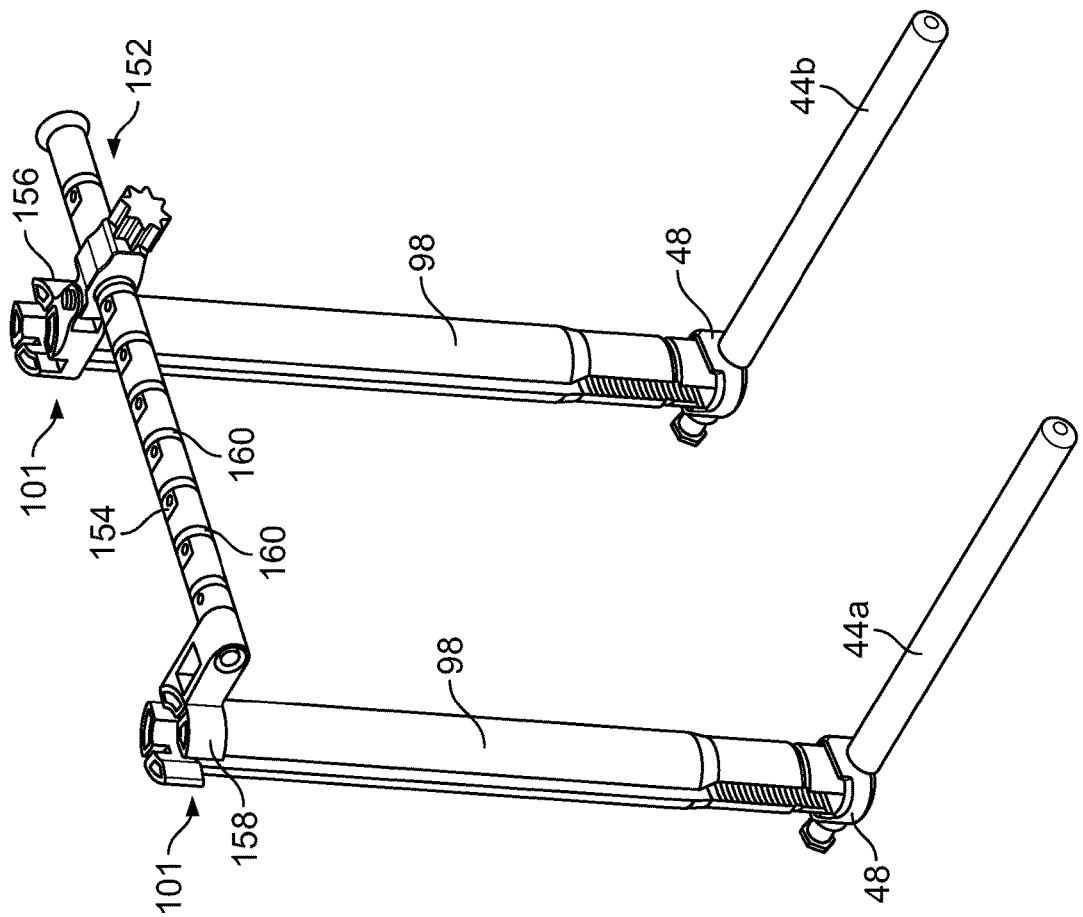
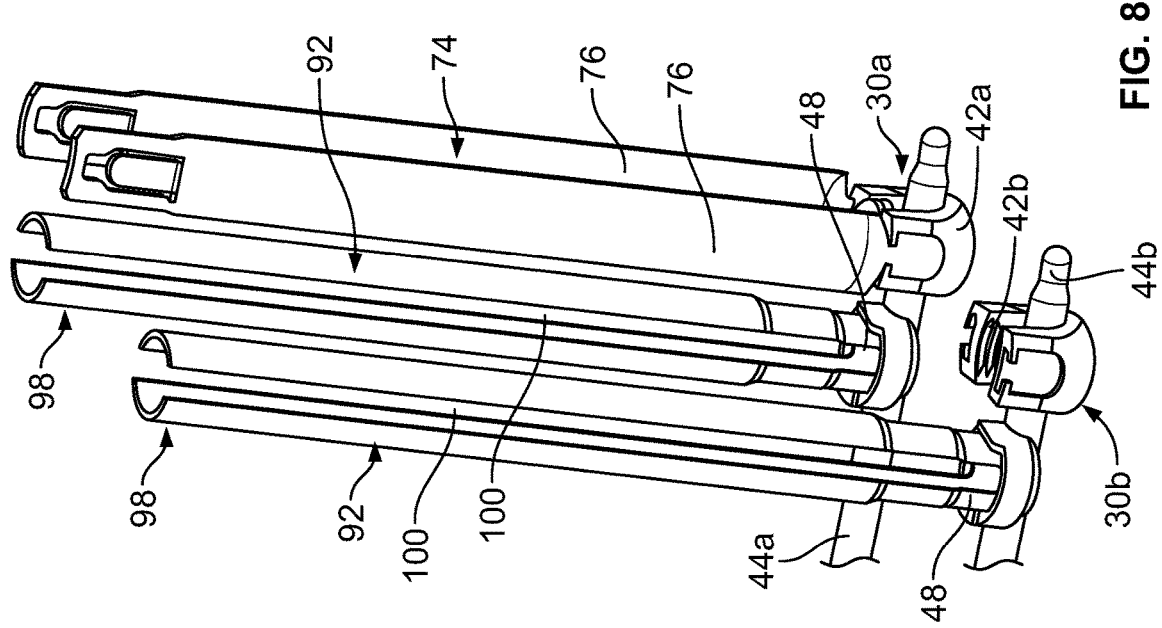

PERCUTANEOUS SPINAL CROSS LINK SYSTEM AND METHOD

CROSS-REFERENCE TO RELATED APPLICATIONS

This application is a continuation of U.S. application Ser. No. 14/201,213, filed on Mar. 7, 2014, which application claims the benefit of the filing date of U.S. Provisional Patent Application No. 61/782,278 filed Mar. 14, 2013, the disclosures of which are hereby incorporated herein by reference.

BACKGROUND OF THE INVENTION

The present invention relates to the percutaneous insertion of spinal fusion implants into the body of a patient and the affixation of those implants to the spine.

Pedicle screw fixation constructs have been in use for decades in order to fuse adjacent vertebral segments to improve spinal stability or correct certain spinal deformities. Older approaches for inserting these fixation constructs involved open procedures, in which relatively large skin incisions were created to expose a substantial portion of the patient's spinal column, in order to allow for insertion of the pedicle screws and manipulation of spinal rods through openings in pedicle screws, such openings typically being in heads of the screws.

Over time, less invasive approaches have been developed. Typically, in such approaches, pedicle screws are inserted into the pedicles of adjacent vertebrae of a patient's spine through individual percutaneous incisions corresponding to the pedicle screws. Fixation or fusion rods are then inserted into the body through one of those incisions, or through an additional incision adjacent to the most cephalad or caudal pedicle screw, and the rod is rigidly connected to the heads of the pedicle screws such that the rod extends along the longitudinal axis of the spine (i.e., along the cephalad/caudal direction) in order to fix the relative positions of the adjacent vertebrae to which the rod is connected. In some such minimally invasive procedures, a percutaneous access device (e.g., a cannula or portal) is connected to each of the pedicle screws and extends through the respective percutaneous incision. Such percutaneous access devices provide a pathway through the tissue from each incision to the respective pedicle screw, in order to aid in the insertion of a spinal rod. Examples of such percutaneous access devices are described in commonly-assigned U.S. Pat. No. 7,955,355 ("the '355 patent") and U.S. Pat. No. 8,002,798 ("the '798 patent"), the entireties of which are hereby incorporated by reference herein as if fully set forth herein.

Although considerable effort has been devoted in the art to optimization of such minimally invasive systems, still further improvement would be desirable.

BRIEF SUMMARY OF THE INVENTION

One aspect of the present invention provides a connector for securing a cross bar to a spinal fusion construct. The connector according to this aspect of the invention desirably includes a rod receiving portion and a cross bar receiving portion. The rod receiving portion is desirably adapted to receive a spinal fusion rod of a spinal fusion construct therein, and the cross bar receiving portion desirably has a receptacle therein. The receptacle of the cross bar receiving portion is desirably adapted to receive a cross bar therein in an orientation generally perpendicular to the spinal fusion rod when the spinal fusion rod is received within the rod receiving portion.

According to one aspect of the invention, the receptacle of the cross bar receiving portion is preferably defined between a first arm and a second arm. According to another aspect of the invention, the arms preferably include inwardly facing threads along at least a portion of the receptacle, and the receptacle is preferably adapted to receive a threaded blocker in engagement with the threads. According to a further aspect of the invention, the rod receiving portion of the connector preferably includes a slot adapted to receive the spinal fusion rod therethrough, and the slot is preferably defined between a first arm and a second arm. According to yet a further aspect of the invention, the first and second arms defining the slot are preferably adapted to deflect relative to one another when the spinal fusion rod is inserted into the slot.

Further aspects of the invention provide a connector assembly for securing a cross bar to a spinal fusion construct. The connector assembly according to this aspect of the invention desirably includes a cannula and also desirably includes a connector in accordance with any of the aspects of the invention described above. A distal end of the cannula is desirably connected to the connector such that a proximal end of the cannula extends through an incision in the skin of a body of a patient when the spinal fusion rod is received within the rod receiving portion of the connector and when the spinal fusion construct is implanted in a spine of the patient.

According to one aspect of the invention, the cannula is preferably defined by a plurality of blades, each of which preferably has a distal end detachably connected to the cross bar receiving portion of the connector. According to another aspect of the invention, the blades are preferably each integrally formed with the cross bar receiving portion of the connector and detachably connected thereto at a frangible portion. According to yet another aspect of the invention, the cannula preferably includes an inner surface having threads for engaging a threaded blocker along at least a distal portion of the cannula.

Yet further aspects of the invention provide a system for securing a cross bar to a spinal fusion construct. The system according to this aspect of the invention desirably includes a dilator and also desirably includes a connector assembly in accordance with any of the aspects of the invention described above. The dilator is desirably adapted to define a pathway between the incision in the skin of the patent and the spinal fusion rod of the spinal fusion construct implanted in the spine. The pathway is desirably adapted to receive the connector assembly through it.

According to one aspect of the invention, the system preferably includes a connector inserter having a shaft, the distal end of which is preferably adapted to engage the cross bar receiving portion of the connector while the shaft is received within and extends along the cannula of the connector assembly.

According to another aspect of the invention, the system preferably includes a linkage and also preferably includes a plurality of the connector assemblies in accordance with any of the aspects of the invention described above. According to this aspect of the invention, the linkage is preferably adapted to simultaneously connect to the proximal end of each of the cannulas of the connector assemblies while the spinal fusion rod is received within the rod receiving portions of the connectors and while the spinal fusion construct is implanted in a spine of the body.

According to another aspect of the invention, the system preferably includes a drill having an elongated extender. According to this aspect of the invention, the elongated extender is preferably adapted to be received within the cannula of the connector assembly. A distal end of the extender is preferably connected to a drill bit such that the drill bit extends generally perpendicularly to the extender.

According to another aspect of the invention, the system preferably includes a cross bar inserter, the distal end of which preferably has a connection structure operable to selectively secure and release the cross bar to it. According to yet another aspect of the invention, the system preferably includes a persuader having a tubular member adapted to receive the cannula of the connector assembly inside of it.

According to another aspect of the invention, the cannula of the connector assembly is preferably defined by a plurality of blades. According to this aspect of the invention, each of the blades is preferably integrally formed with the cross bar receiving portion of the connector. Each of the blades also preferably has a distal end detachably connected to the cross bar receiving portion of the connector at a frangible portion. The system preferably includes a blade remover having a channel adapted to receive one of the blades.

Yet further aspects of the invention provide a method for securing a cross bar to a spinal fusion construct. The method according to this aspect of the invention desirably includes forming a minimally invasive pathway between an incision in the skin of a patient and a spinal fusion rod of a spinal fusion construct implanted in a spine of the patient. The method desirably also includes passing a connector through the pathway and attaching the connector to the spinal fusion rod. The connector desirably has a cross bar receiving portion adapted to receive a cross bar therein in an orientation generally perpendicular to the spinal fusion rod.

According to one aspect of the invention, the method preferably includes maintaining the minimally invasive pathway with a first cannula, the distal end of which is preferably connected to the cross bar receiving portion of the connector. According to another aspect of the invention, the method preferably includes inserting the cross bar into the body of the patient along the first cannula and through a slot along the first cannula.

According to another aspect of the invention, the method preferably includes advancing the cross bar towards the cross bar receiving portion of the connector. Such advancement is preferably performed by rotatably advancing a threaded blocker along a threaded portion of the first cannula.

According to another aspect of the invention, the method preferably includes detaching a plurality of blades defining the first cannula from the cross bar receiving portion of the connector. According to a further aspect of the invention, the step of detaching the blades preferably includes breaking the blades away from the cross bar receiving portion of the connector.

According to another aspect of the invention, the method preferably includes forming a second minimally invasive pathway between a second incision in the skin of the patient and a second spinal fusion rod of the spinal fusion construct. The method according to this aspect of the invention preferably also includes passing a second connector through the second pathway and attaching the second connector to the second spinal fusion rod. The second connector preferably has a cross bar receiving portion which is adapted to receive the cross bar therein in an orientation generally perpendicular to both the spinal fusion rod and the second spinal fusion rod. The method according to this aspect of the invention preferably also includes maintaining the second minimally invasive pathway with a second cannula, the distal end of which is preferably connected to the cross bar receiving portion of the second connector.

According to another aspect of the invention, the method preferably includes attaching a linkage to the proximal ends of the first and second cannulas. According to a further aspect of the invention, the method preferably includes forming an opening in a spinous process of the spine with a drill which is inserted along the minimally invasive pathway.

BRIEF DESCRIPTION OF THE DRAWINGS

FIGS. 6A-B are sectional views of portions of an integrated connector of FIG. 5.

FIG. 8 is a perspective view of a plurality of the integrated connectors of FIG. 5 assembled with a portion of a spinal fusion construct in accordance with an embodiment of the present invention.

FIG. 9 is a perspective view of a linkage assembled with integrated connectors in accordance with an embodiment of the present invention.

DETAILED DESCRIPTION

Where reference is made herein to directional terms such as "proximal," "proximal most," "distal," and "distal most,"

it is to be understood that "proximal" and "proximal most" refer to locations closer to a user or operator of the device or method being described and that "distal" and "distal most" refer to locations further from a user or operator of the device or method being described.

Figure 1:
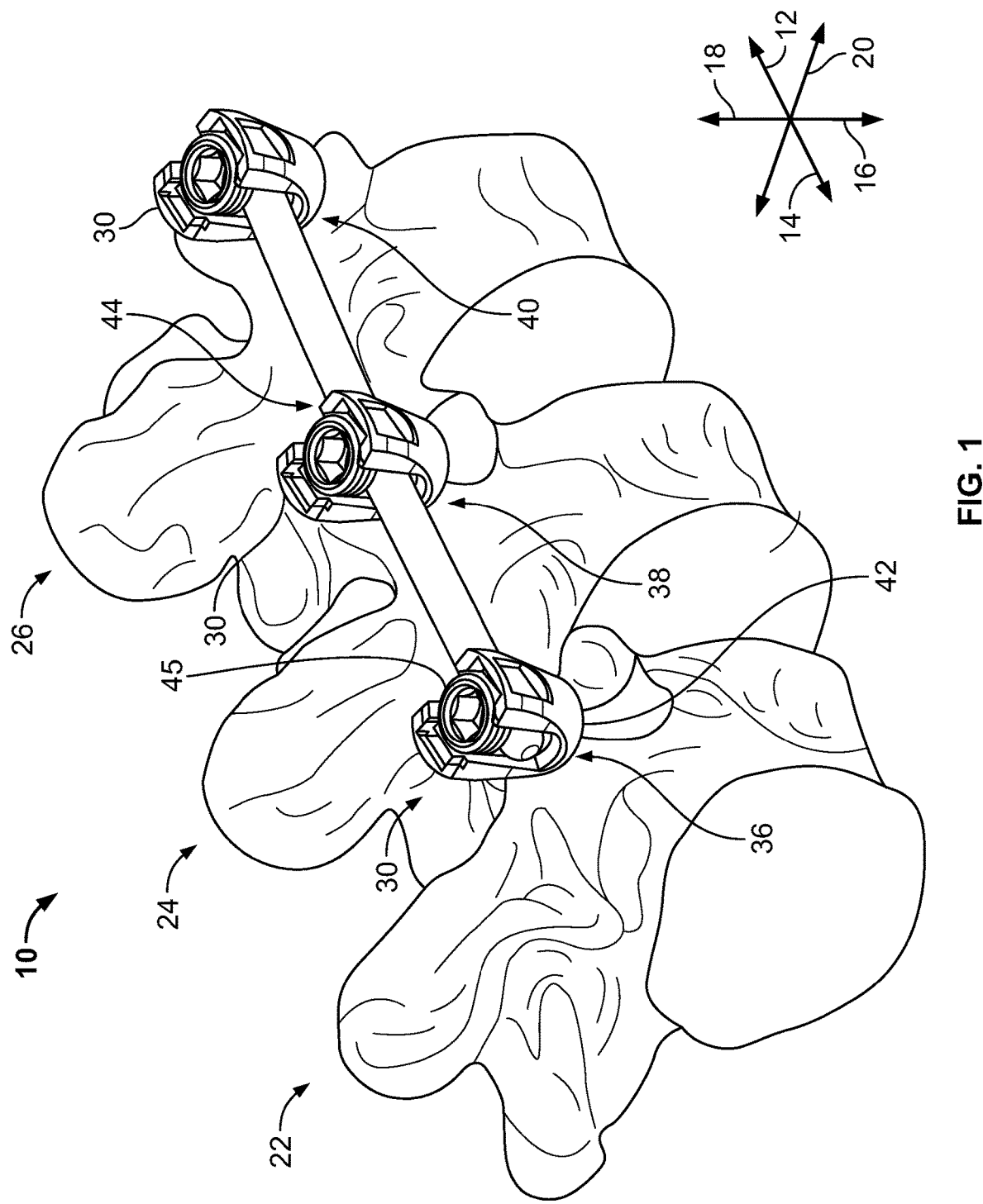
FIG. 1 is a perspective view of a portion of a spine with a prior art spinal fusion construct connected thereto.

Referring to FIG. 1, a perspective view illustrates a portion of a spine 10. FIG. 1 illustrates only the bony structures; accordingly, ligaments, cartilage, and other soft tissues are omitted for clarity. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane (i.e., plane of symmetry that separates left and right sides from each other) of the spine 10, and "lateral" refers to a position or orientation relatively further from the sagittal plane.

As shown, the spine 10 illustrated in FIG. 1 includes a first vertebra 22, a second vertebra 24, and a third vertebra 26. Connecting elements 30 of a spinal fusion construct are connected to respective pedicles 36, 38, 40 on the right side of the respective first, second, and third vertebrae 22, 24, 26. The connecting elements 30 each include a pedicle screw (not shown) implanted in the respective pedicles 36, 38, 40 and a cage 42 for receiving a spinal fusion rod 44 therein. The cages 42 may be polyaxially coupled to the respective pedicle screws. Each connecting element 30 may also include a set screw 45 for securing the rod 44 within the cage 42. The connecting elements 30 may have the same structure as the connecting elements described in the '798 patent, and the connecting elements 30 and the rod 44 may have been percutaneously inserted in the same manner as described in that patent. That is, the connecting elements 30 may have been inserted through separate incisions with the help of guide wires and/or dilators, and the rod 44 may have been inserted with the help of cannulas secured to the connecting elements 30.

Figure 2:
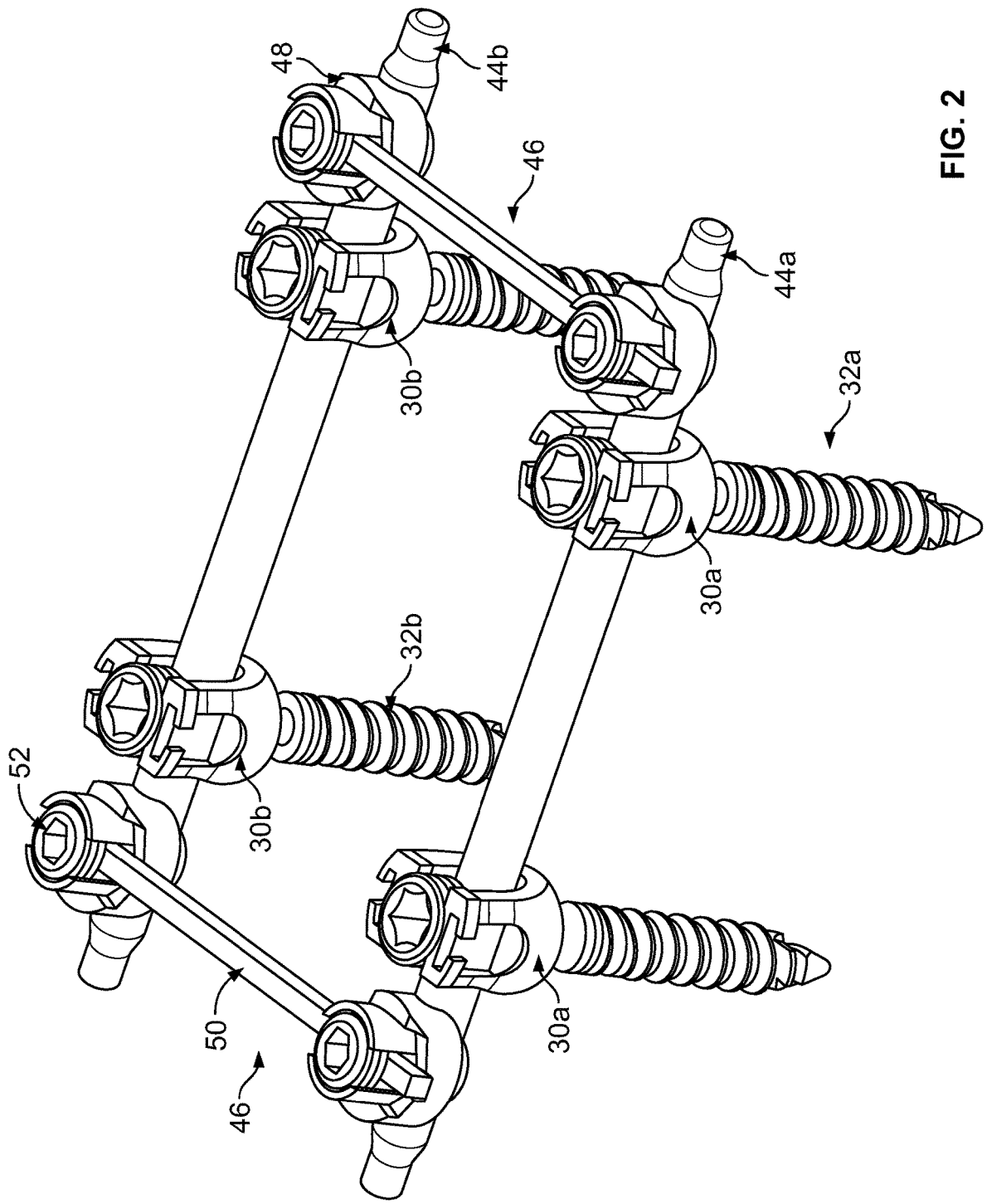
FIG. 2 is a perspective view of a construct of spinal fusion system components in accordance with aspects of the present invention.

Although only one construct on one side (i.e., the right side) of the spine 10 is illustrated in FIG. 1, another similar spinal fusion construct could be connected to pedicles on the other side of the spine in a similar manner, such that the rods 44 extend generally parallel to one another along the longitudinal axis of the spine. As shown in FIG. 2, a construct in accordance with the present invention may include a plurality of connecting elements 30a with an associated rod 44a extending generally parallel to a plurality of connecting elements 30b with an associated rod 44b. Although the spine is not illustrated in FIG. 2, the construct illustrated in FIG. 2 would preferably be connected to the spine such that the pedicle screws 32a of connecting elements 30a would be implanted in pedicles on one side of the longitudinal axis of the spine and the pedicle screws 32b of the connecting elements 30b would be implanted in pedicles on the other side of the longitudinal axis of the spine, such that the rods 44a and 44b extend generally parallel to the longitudinal axis of the spine with the spinous processes of the spine extending between the rods 44a and 44b.

In accordance with embodiments of the present invention, cross links 46 may extend between and be connected to both rods 44a and 44b. Desirably such cross links 46 help to stabilize and increase rigidity of the spinal fusion construct. The cross links 46 may include connectors 48 secured to each rod 44a,b and cross bars 50 received within and secured to the connectors 48 by blockers 52, as discussed in more detail below. A system and method for percutaneously installing such cross links 46 into a spinal fusion construct follows below.

After two generally parallel constructs of connecting elements 30 and rods 44 have been installed on each side of the spine, for example with the systems and methods described in the '798 patent, the cross links 46 may then be installed. First, the surgeon may determine at which locations along the rods 44 the cross links 46 are to be located. Although the connectors 48 of the present invention are desirably structured so as to be positionable at any location along the rods 44, in some preferred spinal fusion constructs in accordance with the present invention the connectors 48 may be located close to the connecting elements 30. It is believed that such placement of the cross links 46 may increase the stability of the spinal fusion construct.

Figure 3C:
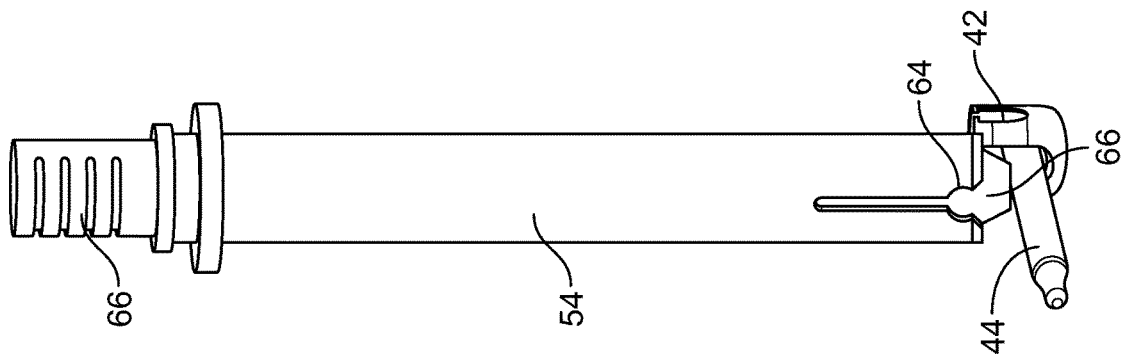
FIG. 3C is a perspective view of an assembly of the components of FIGS. 3A and 3B.
Figure 3B:
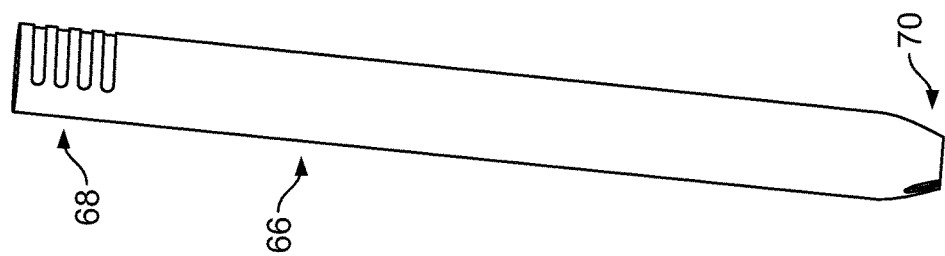
FIGS. 3A-B are perspective views of components of a dilation system in accordance with an embodiment of the present invention.
Figure 3A:
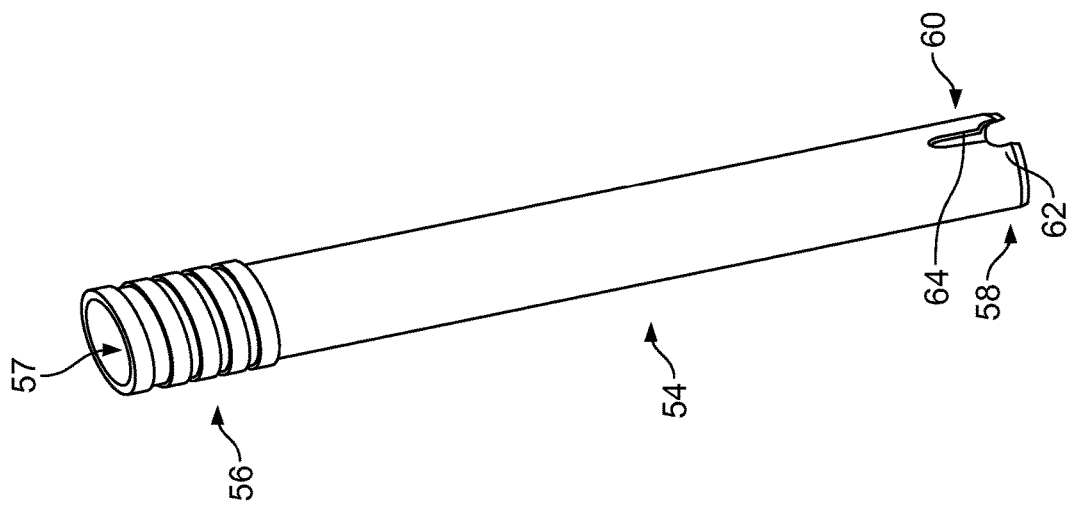

After the desired locations for the connectors 48 have been determined, the body tissue between the skin and each of those locations may be dilated. In one embodiment, the dilation may be performed by inserting a dilation system including a generally tubular dilator 54, as shown in FIG. 3A, through an incision in the skin to the desired location along the rod 44. The dilator 54 has a proximal end 56 and a distal end 58 and defines a passageway 57 therealong. The distal end 58 may have an attachment portion 60 for attachment to the rod 44. For example, the attachment portion 60 may include a recess 62 shaped to receive at least a portion of the rod 44 therein. As shown in FIGS. 3A and 3C, the recess 62 may be partially cylindrical and open to the distal end 58 to receive the rod 44. In order to provide a more stable connection to the rod 44, the attachment portion 60 may be structured to snap onto the rod 44 by deforming when the rod 44 is received within the recess 62. In such an embodiment, a slot 64 may be provided to facilitate such deformation. To ease the insertion of the dilator 54, in some embodiments of the dilation system, a pathway between the skin incision and the desired location along the rod 44 may be sequentially dilated by a series of successively larger dilators inserted one over another, for example as discussed in the '798 Patent, after which the dilator 54 may be inserted over the last of such dilators. In other embodiments of the dilation system, a single inner dilator 66, as shown in FIG. 3B, may be inserted along the pathway, after which the dilator 54 may be inserted over the inner dilator 66, as shown in FIG. 3C. The inner dilator 66 may be generally tubular structure sized to be closely received within the dilator 54 and having a proximal end 68 and a distal end 70. In some embodiments, the distal end 70 may be tapered, as shown in FIG. 3B, in order to gently spread the tissue apart along the pathway as the inner dilator 66 is inserted.

Figure 4B:
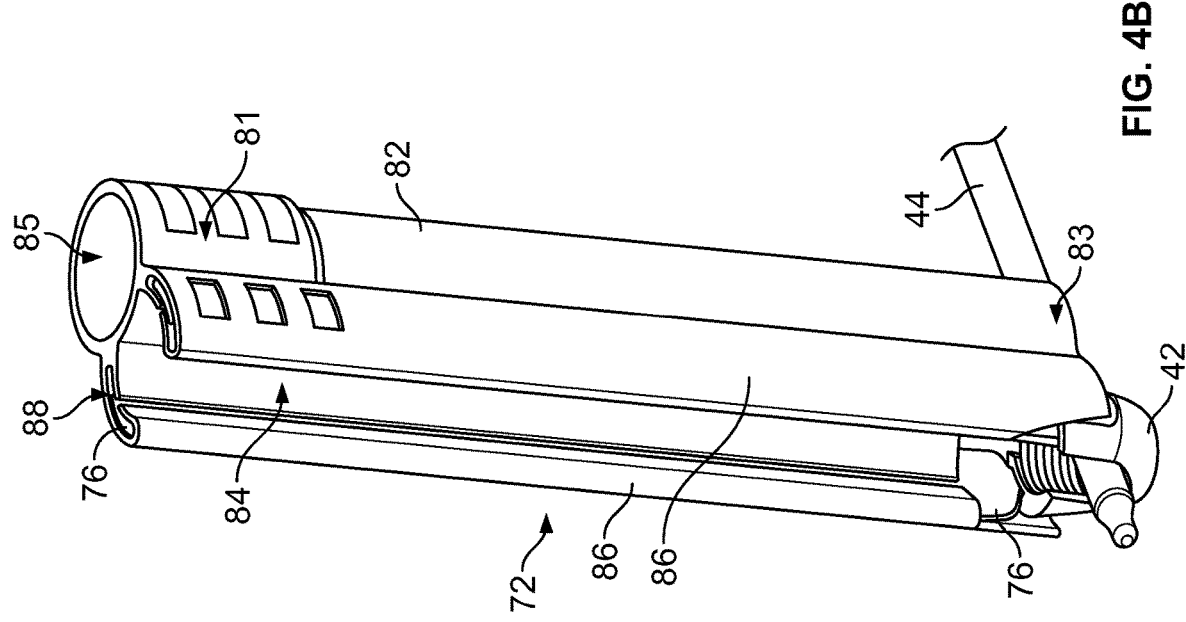
FIG. 4B is a perspective view of a component of a dilation system in accordance with another embodiment of the present invention assembled with the portion of the spinal fusion construct of FIG. 4A.
Figure 4A:
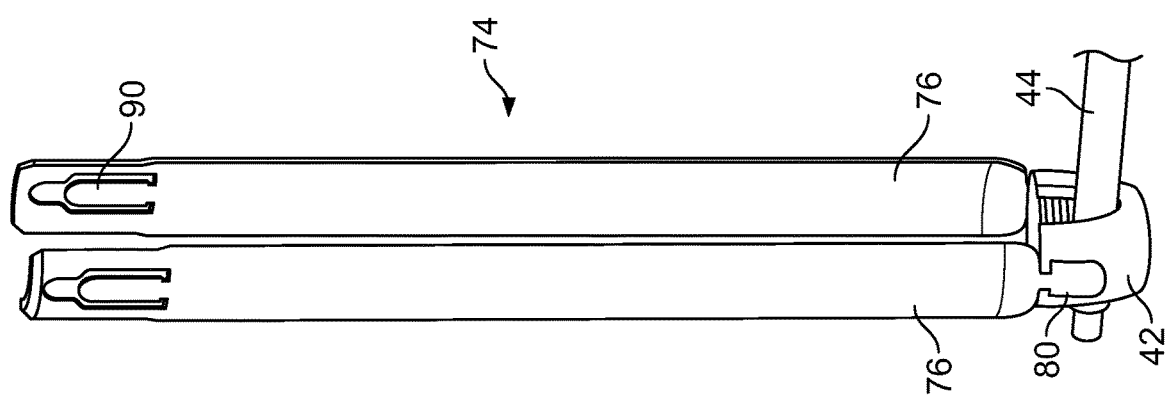
FIG. 4A is a perspective view of a portion of a prior art spinal fusion construct having a percutaneous access device connected thereto.

Another embodiment of a dilation system may include a dilator 72, as shown in FIG. 4B, which may be structured to engage a percutaneous access device connected to one of the connecting elements 30. The percutaneous access device may be in the form of those described in the '355 patent and the '798 patent. For example, as shown in FIG. 4A, the percutaneous access device may be a cannula 74 defined by a two blades 76 connected to opposing sides of the cage 42. The blades 76 may be separately formed from and detachably connectable to the cage 42 of the connecting element 30 by a distal tab 80, as described in certain embodiments of the '798 patent. Alternatively, the cannula 74 may be defined by blades that are integrally formed with the cage 42 and connected thereto by frangible portions (e.g., reduced thickness portions, which may be defined by grooves formed in either or both of the interior and exterior surfaces of cannula at the junction between the blades and the cage), whereby the blades are detachable from the cage 42 breaking the blades away from the cage 42 at the frangible portions. As shown in FIG. 4B, the dilator 72 has a proximal end 81 and a distal end 83 and defines a passageway 85 therealong, and the dilator 72 may include a generally tubular cannula 82 and an attachment structure 84 constructed to engage the blades 76. The attachment structure 84 may include a plurality of receivers 86 extending laterally from the cannula 82, each of the receivers 86 having a channel 88 therealong shaped to receive one of the blades 76 therein. The dilator 72 may be inserted into the body by inserting the proximal ends 90 of the blades 76 into the channels 88 of the receivers 86 at the distal end 83 of the dilator and advancing the dilator 72 distally through the body tissue. During the advancement, the cannula 82 of the dilator may first pass through an incision in the skin, such as an incision adjacent to the cannula 74 defined by the blades 76, and then may progress distally through the body tissue to a desired location along the rod 44, such as a location adjacent to the cage 42. To ease the insertion of the dilator 72, in some embodiments of the dilation system, a pathway between the skin incision and the desired location along the rod 44 may be dilated in advance of the movement of the cannula 82 along that pathway. For example, a dilator (not shown) having a tapered distal end, such as a dilator structured similarly to the inner dilator 66 of FIG. 3B, may be inserted along the pathway in advance of the cannula 82. In one example, such a dilator may be received within the passageway 85 of the cannula 82 with the tapered distal end of the dilator projecting distally of the cannula 82 so as to gently spread the tissue apart along the pathway as the dilator 72 is inserted.

The body tissue between the skin and each of the desired locations for the connectors 48 may be dilated using one or a combination of dilation systems, such as those illustrated in FIGS. 3A-C and 4B. In order to prepare for the insertion of the connectors 48 along the pathways defined by those dilation systems, one or more tools may be used to push tissue away from the desired locations for the connectors 48. For example, an elongate tool (not shown) may be inserted along the passageways 57, 85 defined by the dilators 54, 72, and the distal end of such tool may be used to push any tissue away from the desired locations for the connectors 48. The connectors 48 may then be inserted along the passageways 57, 85 to the desired locations along the rods 44.

Figure 5:
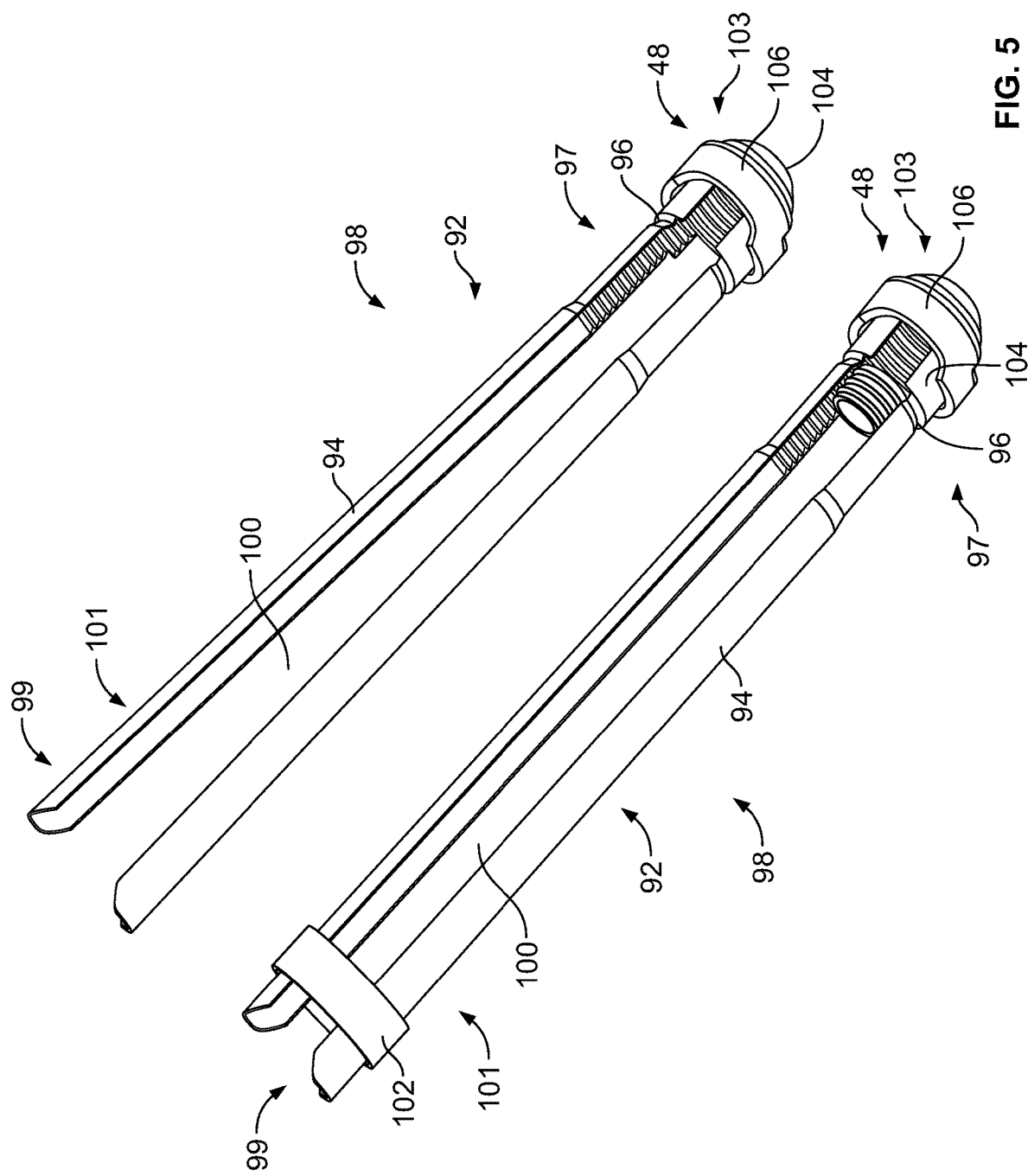
FIG. 5 is a perspective view of two integrated connectors in accordance with embodiments of the present invention.

In one embodiment of the present invention, the connectors 48 may be initially connected to a percutaneous access device before placement within the body. For example, as illustrated in FIG. 5, the percutaneous access device may be in the form of a cannula 92 defined by a two blades 94 extending proximally from opposing sides of the connector 48. In the embodiment illustrated in FIG. 5, the blades 94 may be integrally formed with the connector 48 and connected thereto by frangible portions 96 at the distal end 97 of the cannula 92, thus forming an integrated connector 98 having a proximal end 101 and a distal end 103, with the connector 48 being located at the distal end 103 of the integrated connector 98. However, in an alternative embodiment, the blades 94 may be separately formed from and detachably connectable to the connector 48, such as by distal tabs, as described in certain embodiments of the percutaneous access devices in the '798 patent. The blades 94 may define a pass-through slot 100 extending between them. In other embodiments (not shown), the percutaneous access device may define a slot opening radially outward in only one direction along the cannula 92. In some embodiments, a separately formed ring 102 may be connected to both blades 94, preferably towards the proximal end 99 of the cannula 92, so as to stabilize the blades 94 and resist their becoming detached from the connector 48 prematurely. The ring 102 may be shaped as an annular member having channels formed therethrough for receiving the blades 94 therein. In certain embodiments, the ring 102 may be in the form of abutment member as described in the '798 patent. The ring 102 may be connected to the blades 94 before the integrated connector 98 is inserted into the body or after the integrated connector 98 is connected to the rod 44 within the body.

The connector 48 may include a connecting member 104 and a retaining member 106. The retaining member 106 may be in the form of a separately formed ring encircling a portion of the connecting member 104. FIG. 6A is a cross-sectional view of a portion of an integrated connector 98 towards its distal end 103 with the retaining member 106 removed, the cross-section being taken along a plane perpendicular to the slot 100. The connector 48 includes a rod receiving portion 108 for receiving a rod 44 and a cross bar receiving portion 110 for receiving a cross bar 50. The cross bar receiving portion 110 may include two proximally extending arms 112 defining a receptacle 114 therebetween shaped to receive a cross bar 50 therein in an orientation perpendicular to the longitudinal axis 116 of the integrated connector 98. The receptacle 114 may be in form of a pass through slot communicating with the slot 100 of cannula 92 at the distal end 97 of the cannula 92. The cannula 92 may include a threaded portion 118 at least along the distal end 97 thereof, and the cross bar receiving portion 110 of the connector 48 may include a threaded portion 120 along the arms 112 thereof. In other embodiments (not shown), the threaded portion 118 of the cannula 92 may not be present while the threaded portion 120 of the connector 48 is present. The arms 112 of the cross bar receiving portion 110 may each be connected to a respective one of the blades 94 at one of the frangible portions 96. The frangible portions 96 may be defined by reduced thickness portions, such as by one or both of interior grooves 122 and exterior grooves 124. The interior and exterior grooves 122, 124 may be substantially aligned with one another along the longitudinal axis of the integrated connector 98, as shown in FIG. 6A, to define the reduced thickness portion of the frangible portion 96.

FIG. 6B is a cross-sectional view of a portion of an integrated connector 98 towards its distal end 103 with the retaining member 106 removed, the cross-section being taken along a plane parallel to the slot 100 and perpendicular to the view of FIG. 6A. The view of FIG. 6B focuses on the rod receiving portion 108 of the connector 48. The rod receiving portion 108 may include two distally extending arms 126 defining a receptacle 128 therebetween shaped to receive a rod 44 therein in an orientation perpendicular to the longitudinal axis 116 of the integrated connector 98 and generally perpendicular to the orientation of the cross bar 50 when the cross bar 50 is received within the cross bar receiving portion 110 of the connector 48. The receptacle 128 may be in form of a pass through slot open to the distal end 103 of the integrated connector 98. The rod receiving portion 108 may be structured to snap onto the rod 44 by deforming when the rod 44 is inserted into the receptacle 128. For example, the arms 126 may deflect away from one another during such insertion. One or more slots 130 extending further into the rod receiving portion 108 from the receptacle 128 may be provided to facilitate such deflection of the arms 126. The opening 132 into the receptacle 128 at the distal end 103 of the integrated connector 98 may also have a chamfer 134 to ease insertion of the rod 44 into the receptacle 128 and initiate the deflection of the arms 126 during such insertion.

The retaining member 106 desirably provides stiffness to the connecting member 104, such as by restraining the arms 126 from deflecting too easily. In that manner, the retaining member 106 desirably helps to secure the connector 48 to the rod 44 by restraining the rod 44 from becoming dislodged from the receptacle 128 when not desired. The retaining member 106, when engaged with and encircling the connecting member 104, may engage the connecting member 104 along engagement surfaces 136. As shown in FIG. 7B, the retaining member 106 may take the form of a generally annular ring encircling the connecting member 104. The retaining member 106 may include proximally-extending, arcuate deviations 138 on opposing sides of the retaining member 106 and aligned with the receptacle 128, so as to not interfere with a rod 44 placed into and extending laterally through the receptacle 128.

Figure 7A:
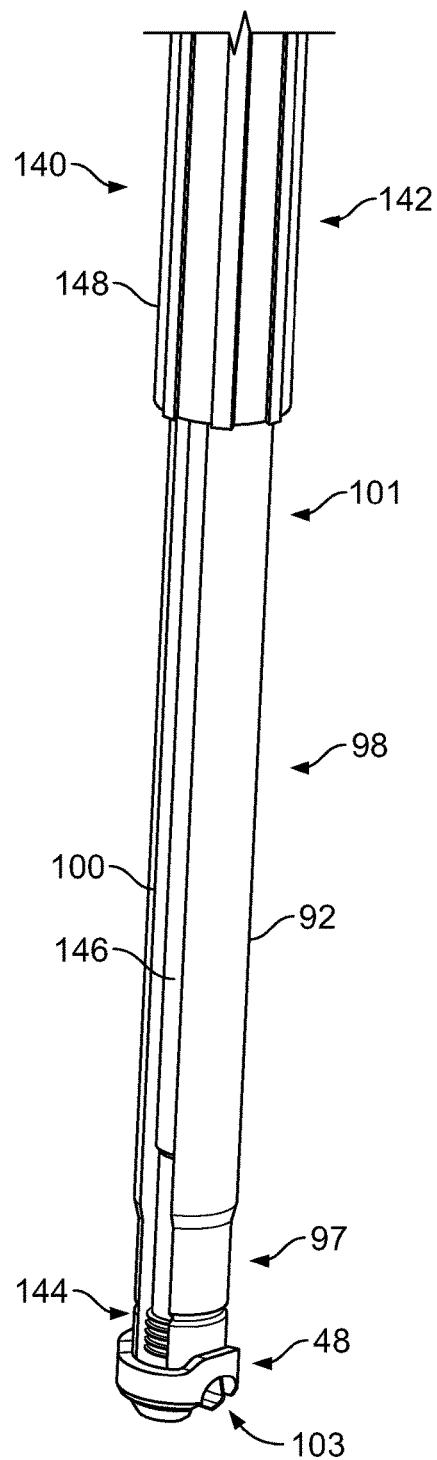
FIG. 7A is a perspective view of an integrated connector of FIG. 5 assembled with a connector inserter in accordance with an embodiment of the present invention.
Figure 7B:
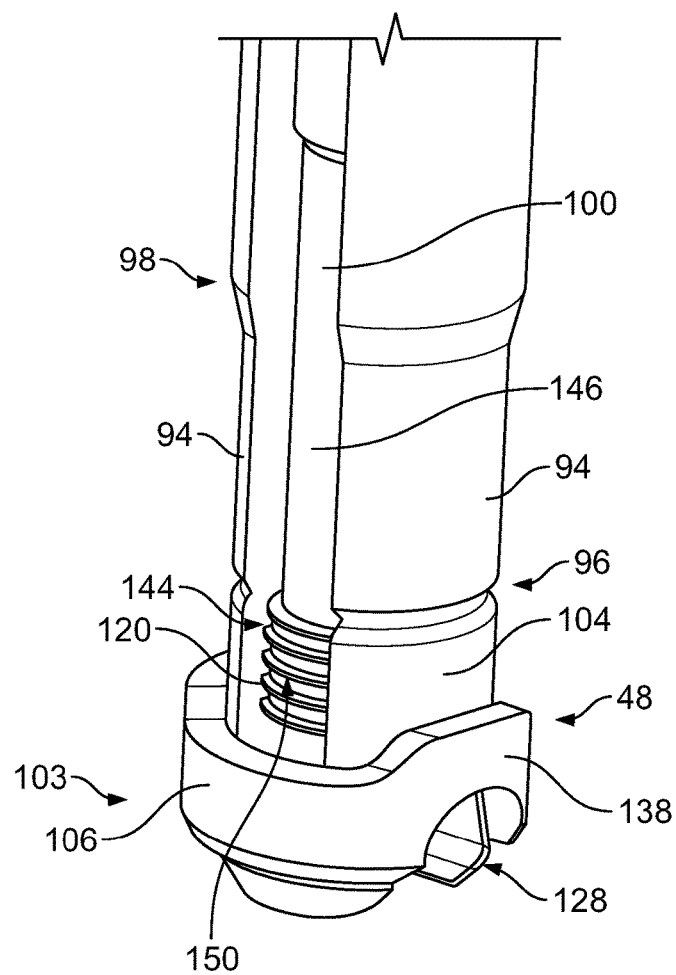
FIG. 7B is an enlarged view of a portion of the assembly of FIG. 7A.

A connector inserter 140, as illustrated in FIGS. 7A-B, may be engaged with an integrated connector 98 in order to assist with the insertion of the integrated connector 98 along the passageways 57, 85 of the dilators 54, 72 and to the desired locations along the rods 44. The connector inserter 140 may have a proximal end 142 and a distal end 144 with an elongate shaft 146 extending therebetween, the shaft 146 being configured to be received within the cannula 92 of the integrated connector 98. The proximal end 142 of the connector inserter 140 may include a handle 148, and the distal end 144 of the connector inserter 140 may include a threaded portion 150 for engagement with the threaded portion 120 of the connector 48, as shown in FIG. 7B. The connector inserter 140 may thus be engaged with the integrated connector 98 by advancing the connector inserter 140 distally within the cannula 92 and rotating the threaded portion 150 of the connector inserter 140 into engagement with the threaded portion 120 of the connector 48. The integrated connector 98 may then be inserted into the body by grasping the handle 148 of the connector inserter 140 and using the connector inserter 140 to manipulate the integrated connector 98 down along the one of the passageways 57, 85 of the dilators 54, 72 until the rod receiving portion 108 of the connector 48 snaps into engagement with the rod 44. The connector inserter 140 may then be removed by rotating the threaded portion 150 of the connector inserter 140 out of engagement with the threaded portion 120 of the connector 48 and withdrawing the connector inserter 140 proximally. After any of the integrated connectors 98 are engaged with the rods 44, the associated dilators 54, 72 may be removed. In some embodiments of the present invention, a ring 102 (see FIG. 5) may be connected to the blades 94 of an integrated connector 98 after the dilator 54, 72 has been removed, and, in other embodiments, a ring 102 may be connected to the blades 94 before the integrated connector 98 is inserted into the body through the dilator 54, 72.

FIG. 8 illustrates two integrated connectors 98 connected to respective rods 44a,b adjacent respective cages 42a,b of respective connecting elements 30a,b. The cannulas 92 of the integrated connectors 98 thus desirably provide percutaneous pathways through body tissue from the connectors 48 to respective incisions in the skin. Although not illustrated in FIG. 8, the connecting element 30a would be implanted in a pedicle on one side of the longitudinal axis of the spine, and the connecting element 30b would be implanted in a pedicle on the other side of the longitudinal axis of the spine, such that the rods 44a and 44b extend generally parallel to the longitudinal axis of the spine with the spinous processes of the spine extending between the rods 44a and 44b. One of the cages 42a in FIG. 8 is illustrated as having two blades 76 of a cannula 74 of a percutaneous access device connected thereto. The slots 100 of the integrated connectors 98 may be generally aligned with one another and may extend generally perpendicular to the rods 44a,b.

In some embodiments, as shown in FIG. 9, a linkage 152 may be connected to the proximal ends 101 of the integrated connectors 98 after the integrated connectors 98 are connected to the respective rods 44a,b. The linkage 152 may include a rail 154 having a movable link 156 slidably connected thereto and having a fixed link 158 rigidly connected to one end. The movable link 156 may have a locked and an unlocked configuration, such that the movable link 156 freely slides along the rail 154 to vary the distance between the two links 156, 158 in the unlocked configuration, and such that the movable link 156 resists movement along the rail 154 in the locked configuration. The rail 154 may include graduations 160 along its length, which graduations 160 may be marked with measurements. Each link 156, 158 may be connected to the proximal end 101 of an integrated connector 98, as shown in FIG. 9, to stabilize the integrated connectors 98. The graduations 160 may also help to determine the distance between the connectors 98, which may assist with the determination of an appropriate length for a cross bar 50 to be inserted between the connectors 48.

Before inserting a cross bar 50 between the connectors 48, a pathway between the connectors 48 may first be created. For example, one or more elongate tools (not shown) may be passed down through the cannulas 92 of one or more of the integrated connectors 98 and through the slots 100 so as to separate or cut away tissue between the connectors 48. In some methods, the spinous processes between the generally parallel rods 44a and 44b may interfere with the desired placement of a cross bar 50. In such cases, a portion of the interfering bone may be removed.

Figure 10:
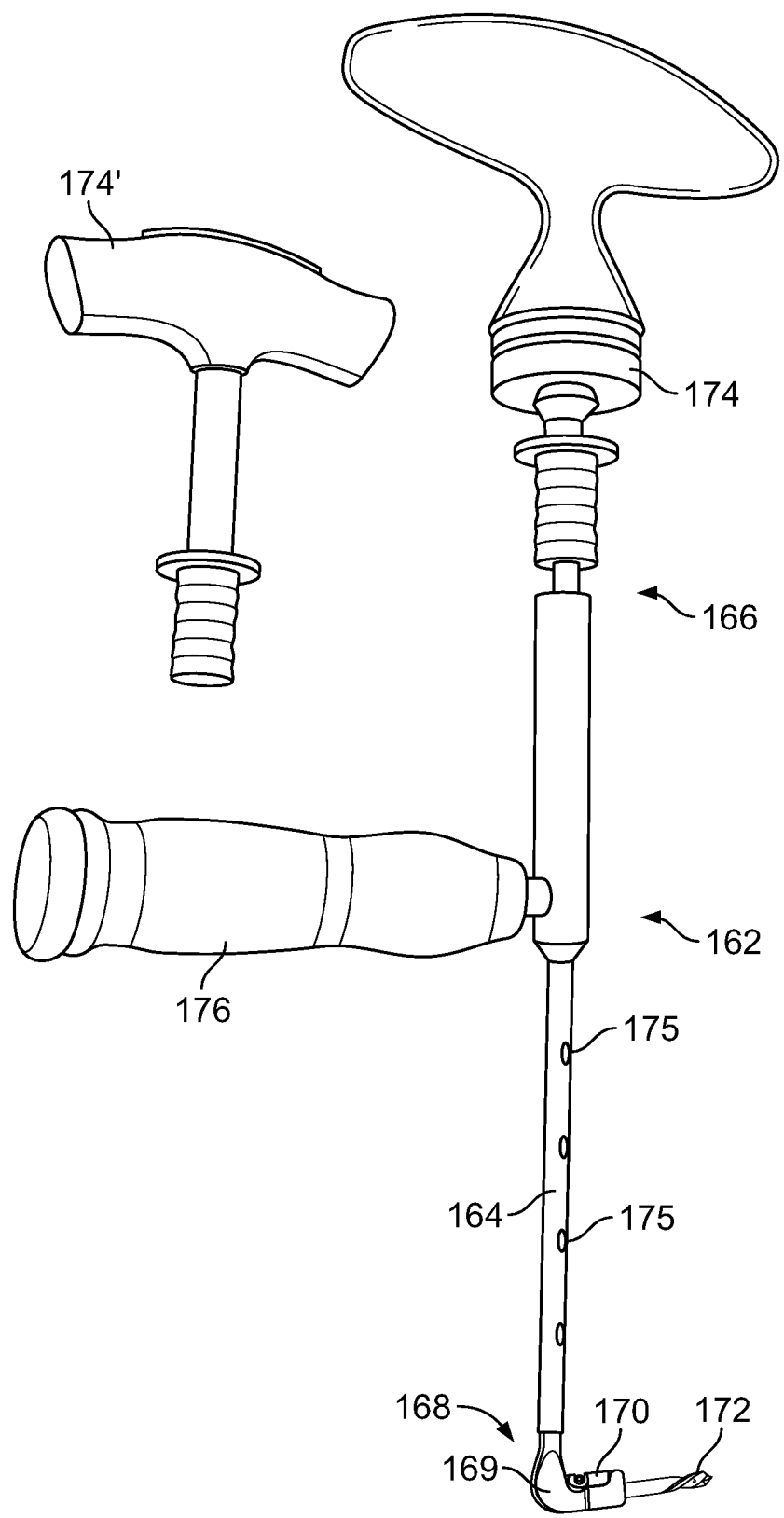
FIG. 10 is a perspective view of a right-angle drill in accordance with an embodiment of the present invention.
Figure 10A:
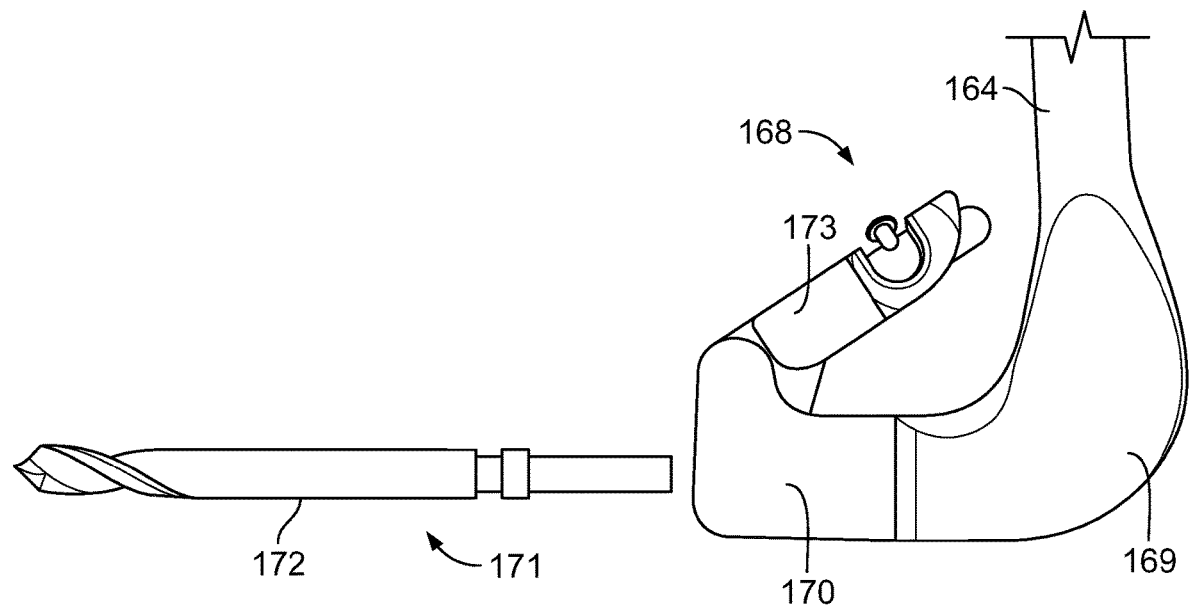
FIGS. 10A-B are perspective views of a portion of the right-angle drill of FIG. 10 in two different configurations.
Figure 10B:
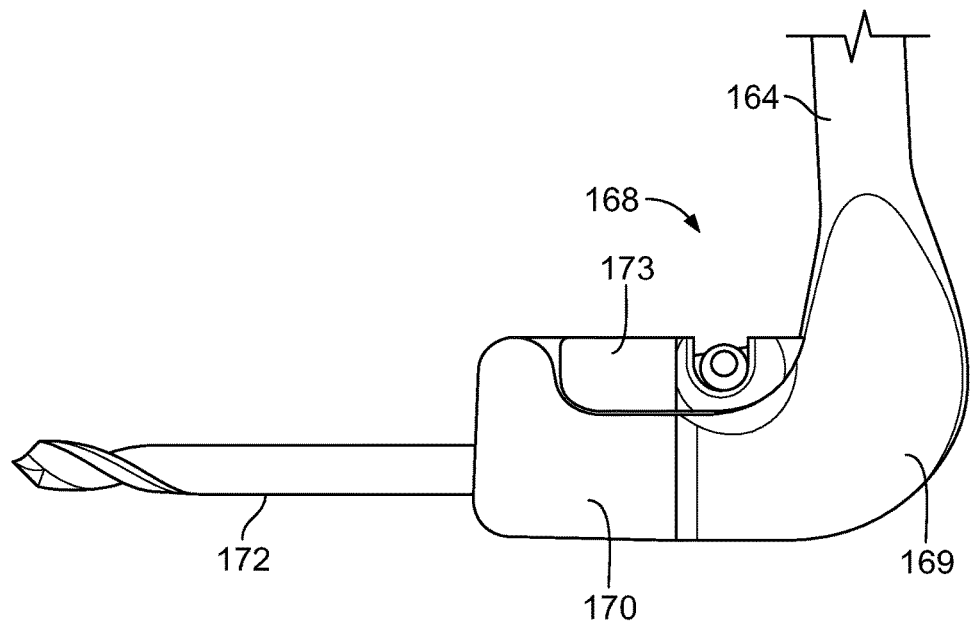

One exemplary tool for performing such bone removal, in accordance with an embodiment of the present invention, includes a right-angle drill 162 as shown in FIG. 10. The right-angle drill 162 may have a proximal end 166 and a distal end 168 and an elongated extender 164 extending therebetween. The distal end 168 of the right angle drill 162 may be structured to sit stably within a receptacle 114 of a cross bar receiving portion 110 of a connector 48. A drill bit 172 may be connected to a drill bit attachment mechanism 170 located at the distal end 168 of the right-angle drill 162. The drill bit attachment mechanism 170 may be connected to the extender 164 by a right-angle bend 169, such that the drill bit 172 extends in a generally perpendicular direction to the extender 164. The drill bit attachment mechanism 170 may be structured for detachable connection to the drill bit 172. For example, as shown in FIG. 10A, the drill bit 172 may include a connection end 171 structured for removable insertion into a receiver opening (not shown) in the drill bit attachment mechanism 170. After the connection end 171 is positioned within the receiver opening, a locking lever 173 may be pivoted downwardly, as shown in FIG. 10B, to secure the drill bit 172 within the drill bit attachment mechanism 170. The extender 164 of the right-angle drill 162 may be structured as a hollow shaft, so that a drive shaft (not shown) may be rotatably received within the extender 164 for driving the rotation of the drill bit 172. The drive shaft may be operably coupled to the drill bit 172 via a mechanism (not shown) for transmitting the rotary motion of the drive shaft through the right-angle bend 169, such as a universal joint, a bevel gear, a worm gear, or any other suitable mechanism. The extender 164 may include one or more holes 175 along its length, which holes 175 may communicate with the interior of the extender 164 for cleaning or other purposes. The proximal end 166 of the extender 164 may be connected to a drive handle 174 for actuating the rotation of the drill bit 172. The drive handle 174 may be detachably connected to a connector (not shown) at the proximal end 166 of the extender 164, which connector is operably coupled to the drive shaft. In some embodiments, other types of drive handles (e.g., drive handle 174' illustrated in FIG. 10) may be interchangeably connected to the connector at the proximal end 166 of the extender 164. The right-angle drill 162 may be structured such that rotation of the drive handle 174 causes rotation of the drill bit 172 (e.g., in a 1:1 ratio, although other ratios may be used). In other embodiments (not shown), the right-angle drill 162 may incorporate a motor for electrical power driven rotation of the drill bit 172. The right-angle drill 162 may include a support handle 176 located along the extender 164 between the proximal end 166 and the distal end 168. The support handle 176 may extend in a generally perpendicular orientation from the extender 164.

In use, an appropriate drill bit 172 may first be connected to the drill bit attachment mechanism 170. For example, based on the approximate distance between the connectors 48 indicated by the graduations 160 of the linkage 152, a drill bit 172 having an appropriate length may be connected to the drill bit attachment mechanism 170. The right-angle drill 162 may then be inserted along a cannula 92 of one of the integrated connectors 98, and the drill bit 172 may extend through a slot 100 of the integrated connector 98 towards a location on a spinous process where the surgeon desires an opening to be formed. The right-angle drill 162 may be positioned such that, at least initially, the distal end 168 rests in the receptacle 114 of the cross bar receiving portion 110 of a connector 48. The drive handle 174 may then be rotated in order to rotate the drill bit 172 and form an opening through the spinous process. Fluoroscopy may be used to help navigate the drill bit 172 within the body, and the perpendicularly extending support handle 176 may be used both to support the right-angle drill 162 and to act as a directional vector, as the support handle 176 may desirably extend generally parallel to the drill bit 172. After one or more openings are formed through one or more spinous processes with the right-angle drill 162, the right-angle drill 162 may be removed from the body.

Figure 11B:
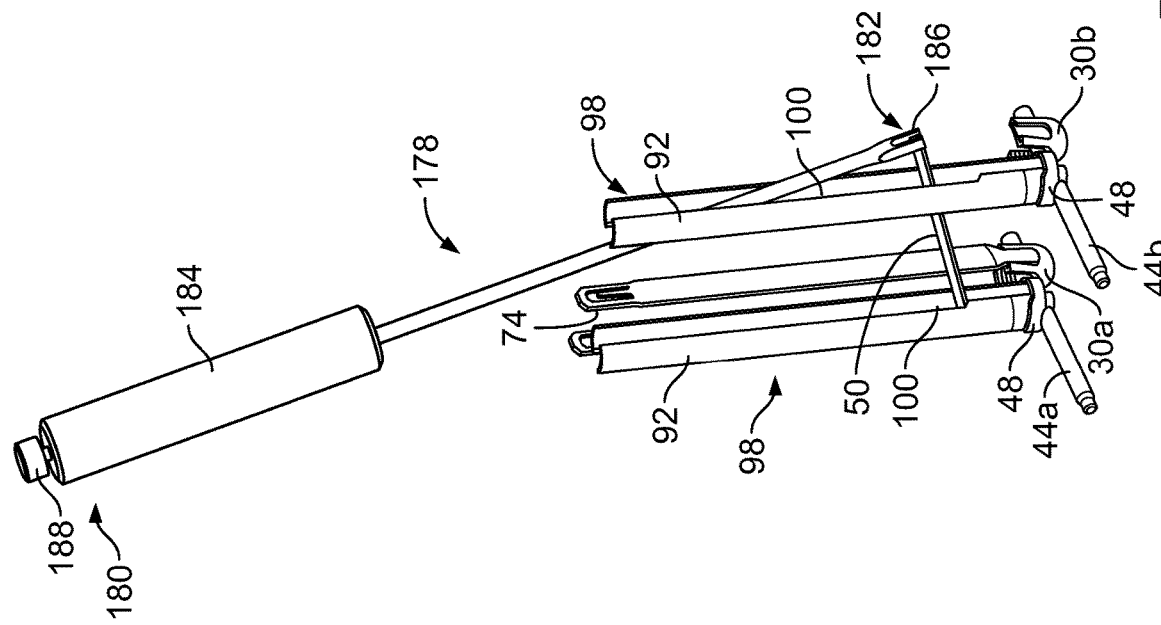
FIG. 11B is a perspective view of a method of insertion of a cross bar into the assembly of FIG. 8.
Figure 11A:
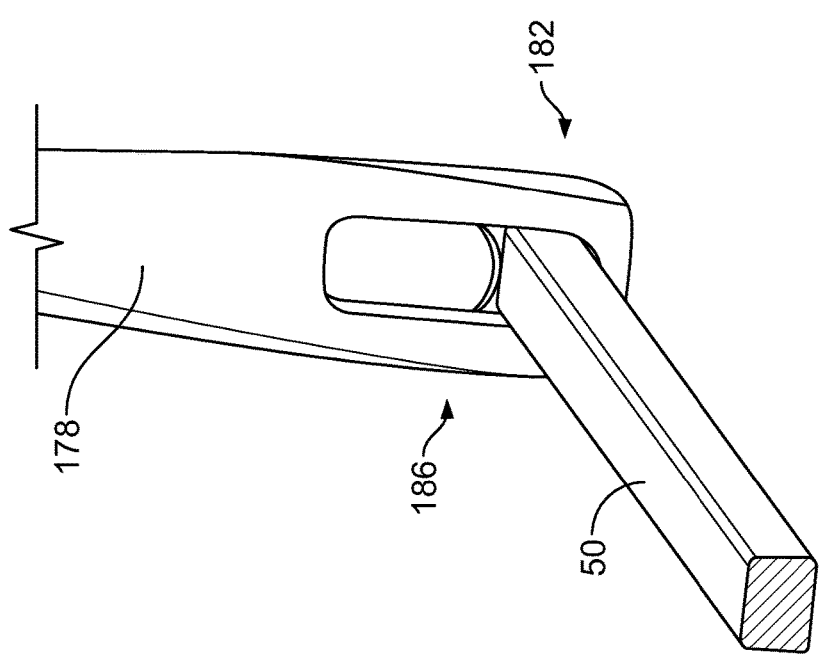
FIG. 11A is a perspective view of a portion of a cross bar inserter connected to a cross bar in accordance with an embodiment of the present invention.

Before a cross bar 50 is inserted into the body and connected between two connectors 48, the cross bar 50 may first be bent and/or cut as needed so that the cross bar 50 is appropriately sized and shaped to extend between the connectors 48. The cross bar 50 may be attached to a cross bar inserter 178, as shown in FIGS. 11A-B, before insertion into the body. The cross bar inserter 178 may be an elongate tool having a handle 184 at a proximal end 180 and a connection structure 186 at the distal end 182 for detachably connecting to a cross bar 50. The proximal end 180 of the cross bar inserter 178 may also include an actuator 188 configured to operate the connection structure 186 so as to selectively secure and release the cross bar 50 to the connection structure 186. Once the cross bar 50 is attached to the cross bar inserter 178, the handle 184 of the cross bar inserter 178 may be grasped and used to manipulate the cross bar 50 down along the cannula 92 of one of the integrated connectors 98, through the slot 100, and across through body tissue (including through an opening in the spinous process, if applicable), as illustrated in FIG. 11B, until the cross bar 50 extends between the integrated connectors 98 in a position proximate the connectors 48 attached to each parallel rod 44a,b.

Figures 12A, 12B:
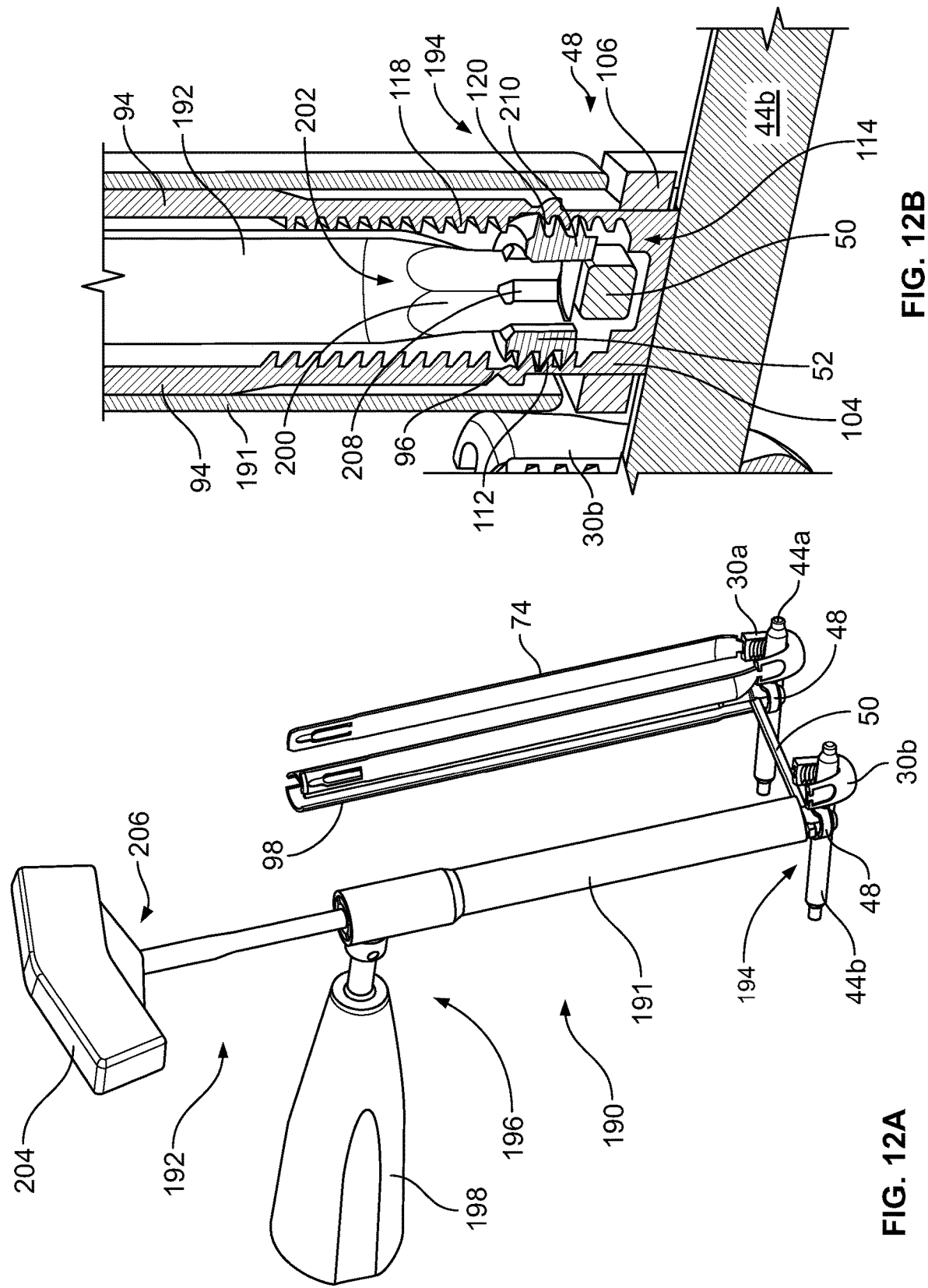
FIG. 12A is a perspective view of a method of persuading the cross bar into the assembly of FIG. 8.
FIG. 12B is a perspective, sectional view of the method of FIG. 12A.

Once the cross bar 50 is positioned proximate the connectors 48, the cross bar 50 may be moved into a final position extending between and simultaneously received by the receptacles 114 of the cross bar receiving portions 110 of each of the connectors 48. The cross bar 50 may be moved into that final position using the cross bar inserter 178. In another alternative, the cross bar 50 may be moved into the final position using either or a combination of a persuader 190 and a blocker inserter 192, as shown in FIGS. 12A-B. The persuader 190 may have a generally tubular member 191 having a distal end 194 and a proximal end 196. The tubular member 191 may be sized to fit over an integrated connector 98 such that the integrated connector 98 is received inside the tubular member 191, as shown in FIGS. 12A-B. A handle 198 may be connected to the tubular member 191 towards its proximal end 196. The blocker inserter 192 may be an elongate tool having a handle 204 at its proximal end 206 and a blocker interface 200 at its distal end 202. The blocker interface 200 may be shaped to engage a correspondingly shaped interface 208 (such as a hexagonally shaped recess) on a blocker 52. The blocker 52 may be an externally threaded component, similar to the set screws 45 of the connecting elements 30 implanted in the pedicles, and the threads 210 of the blocker 52 may be structured to engage the threaded portion 118 towards the distal end 97 of the cannula 92 and the threaded portion 120 of the cross bar receiving portion 110 of the connector 48.

In one embodiment, the handle 198 of a persuader 190 may be grasped and manipulated so that the tubular member 191 is fit over the proximal end 101 of an integrated connector 98 and advanced distally towards the transversely oriented cross bar 50. The distal end 194 of the tubular member 191 may contact the cross bar 50 and push it distally towards and into the final position within the receptacle 114 of the connector 48.

In another embodiment, a blocker inserter 192 may have a blocker 52 placed onto the blocker interface 200 at its distal end 202, after which the blocker inserter 192 may be advanced distally between the blades 94 of the integrated connector 98. When the blocker 52 reaches the threaded portion 118 of the cannula 92, the blocker inserter 192 may be rotated to advance the blocker 52 along the threaded portion 118. Further advancement of the blocker 52 may cause the threads 210 of the blocker 52 to engage and advance along the threaded portion 120 of the connector 48. The blocker 52 may be advanced in this manner until the cross bar 50 is securely captured within the receptacle 114. Desirably, at some point during the distal advancement of the blocker 52, such as during the advancement along the threaded portion 118 or along the threaded portion 120, the blocker 52 may contact the cross bar 50 and push the cross bar 50 distally towards and into the final position within the receptacle 114.

In another embodiment of the present invention, both the persuader 190 and the blocker inserter 192 may be used, as shown in FIGS. 12A-B. For example, the persuader 190 may be used to push the cross bar 50 distally, as described above, until the cross bar 50 is at least within the threaded portion 118 of the cannula 92. After that, the blocker inserter 192 connected to the blocker 52 may be advanced, as described above, to push the cross bar 50 the remaining distance towards and into the final position within the receptacle 114.

In some embodiments, the blocker inserter 192 may be constructed as a torque wrench, such that the torque applied by the blocker interface 200 is limited to a pre-selected amount. In other embodiments, the blocker inserter 192 may not be so constructed, and a separate torque-limiting blocker inserter (not shown) may be provided. In either case, the final tightening of the blocker 52 into the connector 48 so as to secure the cross bar 50 therein may be performed with a torque limiting tool. Such a tool may be set to limit the tightening torque to, for example, 8 Nm (newton-meters).

The cross bar 50 may be released from the cross bar inserter 178, and the cross bar inserter 178 may be removed from the body, at any point after the cross bar 50 is in a desired position within the body. For example, the cross bar inserter 178 may be removed before the cross bar 50 is moved into the final position using either or both of the persuader 190 and the blocker inserter 192. Alternatively, the cross bar inserter 178 may remain attached to the cross bar 50 during the final positioning with the persuader 190 and the blocker inserter 192, preferably in a location out of the way of those tools.

After the various blockers 52 have been finally tightened to secure one or more cross bars 50 within the connectors 48, any insertion tools that remain positioned within the body (including the cross bar inserter 178, persuader 190, and blocker inserter 192) may be removed from the body. The cannula 92 may then be removed from the connector 48. For example, the blades 94 of the cannula may be separately disconnected from the connector 48 and removed from the body. In an embodiment utilizing an integrated connector 98, the blades 94 may be disconnected from the connector 48 by breaking each of the blades 94 away from the connector 48 at the frangible portions 96.

Figure 13:
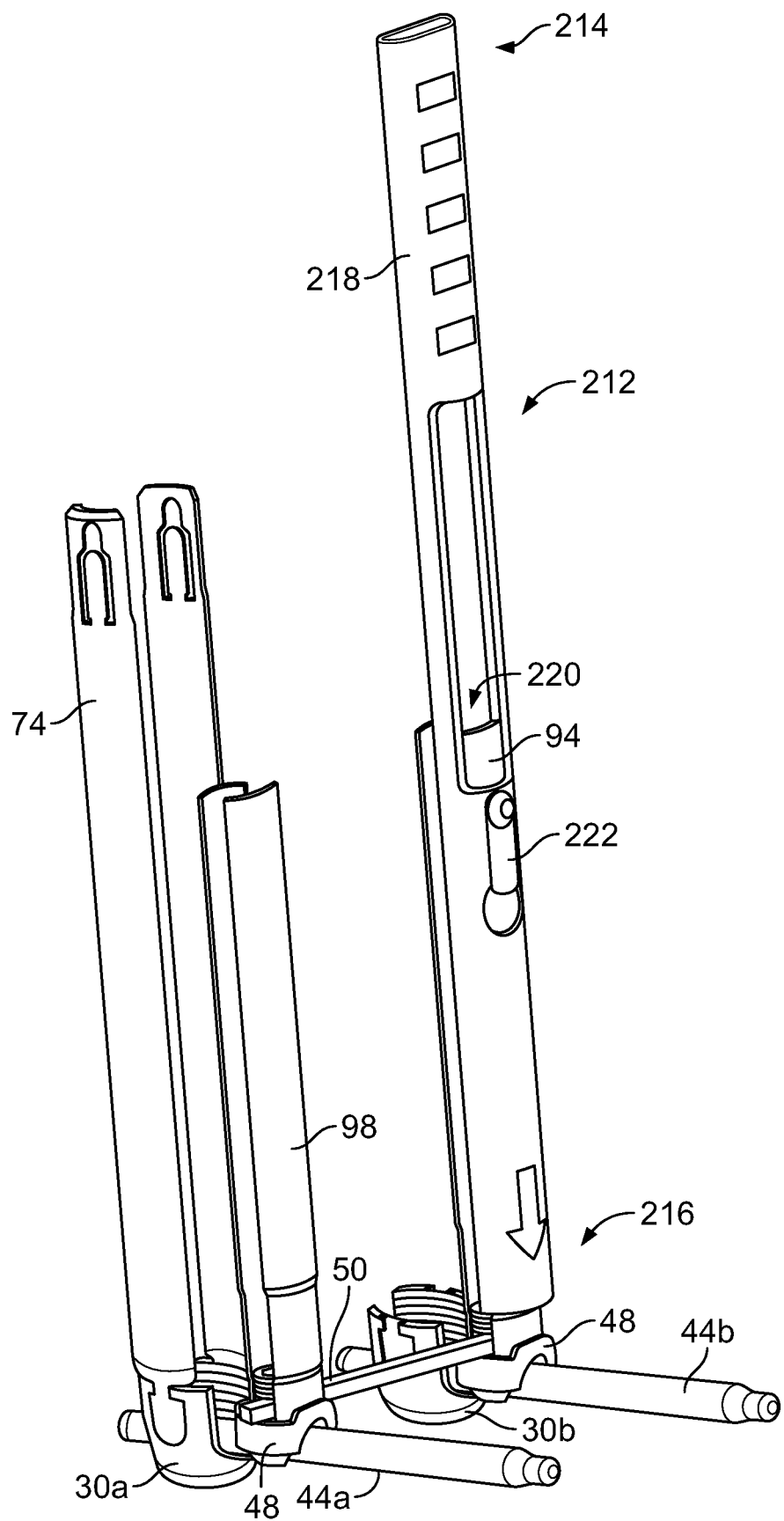
FIG. 13 is a perspective view of a method of removing the blades from the integrated connectors of the assembly of FIG. 8.

One method for breaking the blades 94 of the integrated connector 98 away from the connector 48 is illustrated in FIG. 13. Such a method may include separately engaging each blade 94 with a blade remover 212. The blade remover 212 may be an elongate tool having a proximal end 214 and a distal end 216. The blade remover 212 may include a handle 218 at the proximal end 214 and may have a channel 220 formed therein open to the distal end 216. The channel 220 may be constructed to receive a blade 94 of an integrated connector 98 therein. The blade remover 212 may also include a spring clip 222 in communication with the channel 220 such that the spring clip 222 may securely engage a blade 94 when the blade 94 is positioned within the channel 220, preferably in order to retain the blade 94 within the blade remover 212 after the blade 94 has been detached from the connector 48. The blade remover 212 may also include a release mechanism (not shown) movably engaged within the channel 220 so as to eject the blade 94 from the channel 220 after the detached blade 94 has been removed from the body. In one embodiment, the release mechanism may include a slider received within a longitudinal track along the channel 220, such that distal movement of the slider will push the blade 94 out of the channel 220 at the distal end 216 of the blade remover 212.

In use, the blade remover 212 is engaged to a blade 94 by sliding the blade remover 212 distally over the blade 94 until the blade is received within the channel 220. Using the handle 218, a user may pivot the blade remover 212, and thus the blade 94 received therein, about the frangible portion 96 until the frangible portion 96 fractures, thus disconnecting the blade 94 from the connector 48. The blade remover 212 may then be removed from the body, and desirably the spring clip 222 may retain the blade 94 within the blade remover 212 until the blade remover 212 is removed from the body. After the blade remover 212 is removed from the body, the detached blade 94 may be ejected from the channel 220 by actuating the release mechanism. The blade remover 212 may then be used again by repeating the above steps to remove other blades 94 from the connectors 48.

Although, in the connectors 48 described herein, the rod receiving portion 108 is illustrated as being integrally formed with the cross bar receiving portion 110, in other embodiments of the connectors in accordance with the present invention, the rod receiving portion may be separately formed from the cross bar receiving portion, and both such parts may be coupled together to form the connector. In one such an embodiment, the rod receiving portion and the cross bar receiving portion may be polyaxially coupled together.

Although the connectors 48 described herein are structured for direct engagement with the rods 44, other embodiments of the connectors in accordance with the present invention may be otherwise engageable with portions of the spinal fusion construct. For example, the connector may be structured to straddle the cage 42 of a connecting element 30 while the connector is connected to the rod 44 on each side of the cage 42. In another example, the connector may not be engaged with the rod 44 at all, and may instead, for example, be structured to be directly affixed to the cage 42 of a connecting element 30.

The various components described herein are preferably constructed of materials safe for use in the body. In one embodiment, many of the components, including the components of the integrated connector 98, may be constructed from a titanium alloy.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A dilator for accessing a spinal fusion rod attached to a spine, comprising:
   a generally tubular body having a proximal end and a distal end, the generally tubular body defining a passageway therein extending along a longitudinal axis thereof such that a connector can be passed through the passageway from the proximal end to the spinal fusion rod positionable at the distal end; and
   an attachment structure at the distal end of the generally tubular body, the attachment structure being defined by a partially cylindrical recess extending across the distal end of the generally tubular body transverse to the longitudinal axis, such that the partially cylindrical recess intrudes into the distal end of the generally tubular body to thereby define a concave cylindrical surface and an opposing opening open in a distal direction along the longitudinal axis, the partially cylindrical recess being adapted to mate with the spinal fusion rod by advancing the spinal fusion rod into the opening in a proximal direction along the longitudinal axis, such that the partially cylindrical recess deforms to snap onto the spinal fusion rod and a circular cross section of the spinal fusion rod is received within the partially cylindrical recess of the attachment structure.

2. The dilator of claim 1, wherein the attachment structure includes a slot to facilitate the deformation of the attachment structure when the attachment structure snaps onto the spinal fusion rod.

3. A dilation system, comprising:
the dilator as recited in claim 1; and
at least one inner dilator adapted to be received within the passageway of the dilator, the inner dilator being adapted to spread tissue apart along a pathway to the location proximate the spine before the dilator is advanced along the pathway.

4. The dilation system of claim 3, wherein a distal end of the inner dilator is tapered.

5. A dilator for accessing a location proximate a spine, comprising:
a generally tubular body extending along a longitudinal axis between a proximal end and a distal end, the generally tubular body defining a first passageway therein extending along the longitudinal axis; and
an attachment structure adapted to mate with a percutaneous access device detachably connected to a connecting element for attachment to the spine, the percutaneous access device defining a second passageway therein that extends proximally from the connecting element, wherein the attachment structure is connected to the generally tubular body such that, when the attachment structure is mated with the percutaneous access device, the first passageway defined by the generally tubular body is laterally spaced apart from the second passageway defined by the percutaneous access device.

6. The dilator of claim 5, wherein the attachment structure is positioned alongside the generally tubular body between its proximal and distal ends.

7. The dilator of claim 6, wherein the connecting element is adapted to secure a spinal fusion rod to the spine, and wherein the percutaneous access device is detachably connected to the connecting element and extends proximally therefrom out of the body.

8. The dilator of claim 7, wherein the percutaneous access device comprises two blades positioned adjacent to one another and defining an elongated cannula, and wherein the attachment structure extends laterally from the generally tubular body and receives the blades therein.

9. The dilator of claim 8, wherein the attachment structure includes a plurality of receivers extending laterally from the generally tubular body, each of the receivers having a respective channel therealong shaped to receive a respective blade therein.

10. A dilation system, comprising:
the dilator as recited in claim 5; and
at least one inner dilator adapted to be received within the passageway of the dilator, the inner dilator being adapted to spread tissue apart along a pathway to the location proximate the spine before the dilator is advanced along the pathway.

11. The dilation system of claim 10, wherein a distal end of the inner dilator is tapered.

\* \* \* \* \*